US010658073B2

(12) United States Patent
Bassett, Jr. et al.

(10) Patent No.: US 10,658,073 B2
(45) Date of Patent: May 19, 2020

(54) METHODS AND SYSTEMS FOR INTERPRETATION AND REPORTING OF SEQUENCE-BASED GENETIC TESTS USING POOLED ALLELE STATISTICS

(71) Applicants: QIAGEN Redwood City, Inc., Redwood City, CA (US); QIAGEN GmbH, Hilden (DE)

(72) Inventors: Douglas E. Bassett, Jr., Kirkland, WA (US); Daniel R. Richards, Palo Alto, CA (US); Peer M. Schatz, Duesseldorf (DE)

(73) Assignees: QIAGEN Redwood City, Inc., Redwood City, CA (US); QIAGEN GmbH, Hilden (DE)

( * ) Notice: Subject to any disclaimer, the term of this patent is extended or adjusted under 35 U.S.C. 154(b) by 1015 days.

(21) Appl. No.: 14/460,568

(22) Filed: Aug. 15, 2014

(65) Prior Publication Data
US 2016/0048564 A1 Feb. 18, 2016

(51) Int. Cl.
*G16H 10/20* (2018.01)
*G16B 50/00* (2019.01)

(52) U.S. Cl.
CPC .......... *G16H 10/20* (2018.01); *G16B 50/00* (2019.02)

(58) Field of Classification Search
CPC ........ G16H 50/20; G16H 10/40; G16H 15/00; G16H 20/30; G16H 40/20; G16H 40/63; G16H 40/67; G16H 70/40; G16H 10/20; G16H 30/40; G16H 50/50; G16H 50/70; C12Q 2600/156; C12Q 1/6827; C12Q 1/6883; C12Q 2600/112; G06K 9/628; G16B 40/00; G16B 50/00
See application file for complete search history.

(56) References Cited

U.S. PATENT DOCUMENTS

| | | | |
|---|---|---|---|
| 7,001,736 B1 | 2/2006 | Poirier | |
| 2002/0046054 A1 | 4/2002 | Morand et al. | |
| 2004/0249791 A1 | 12/2004 | Waters et al. | |
| 2010/0063839 A1 | 3/2010 | Alsafadi | |
| 2011/0113002 A1 | 5/2011 | Kane et al. | |
| 2013/0218581 A1 | 8/2013 | Catlett et al. | |
| 2014/0278135 A1 | 9/2014 | Pruss et al. | |
| 2014/0304270 A1 | 10/2014 | Torkamani et al. | |
| 2014/0350954 A1 | 11/2014 | Ellis et al. | |
| 2015/0379193 A1 | 12/2015 | Bassett, Jr. et al. | |
| 2016/0048634 A1 * | 2/2016 | Torkamani ............. | G16B 50/00 707/740 |

FOREIGN PATENT DOCUMENTS

| | | | |
|---|---|---|---|
| CN | 102067142 A | 5/2011 | |
| JP | 2001-188876 A | 7/2001 | |
| JP | 2001-524809 A | 12/2001 | |
| JP | 2002-041657 A | 2/2002 | |
| JP | 2003-108663 A | 4/2003 | |
| JP | 2010-504579 A | 2/2010 | |
| WO | WO 2013/070634 | * 5/2013 | ............. G06F 19/22 |
| WO | WO 2013/070634 A1 | 5/2013 | |
| WO | WO 2013/084121 A2 | 6/2013 | |
| WO | WO 2014/063080 A1 | 4/2014 | |

OTHER PUBLICATIONS

Welter et al. (The NHGRI GWAS Catalog, a curated resource of SNP-trait associations; Nucleic Acids Research 2014, 42, D1001-D1006).*
Written Opinion of the International Searching Authority with Search Report directed to App. No. PCT/US2015/036338, dated Nov. 17, 2015; 15 pages.
U.S. Appl. No. 14/319,986, Bassett et al., "Methods and systems for interpretation and reporting of sequence-based genetic tests,"filed Jun. 30, 2014.
E. Camon: "The Gene Ontology Annotation (GOA) Database: sharing knowledge in Uniprot with Gene Ontology", Nucleic Acids Research, vol. 32, No. 90001, Jan. 1, 2004 (Jan. 1, 2004), pp. 262D-266D.
Office Action directed to related European Patent Application No. 15739372.9, dated May 21, 2019; 10 pages.
Office Action directed to related Japanese Patent Application No. 2017-521064, dated May 22, 2019, with attached English-language translation; 7 pages.
"The NHGRI GWAS Catalog, a curated resource of SNP-trait associations," Nucleic Acides Research, vol. 42, 2014; pp. D1001-D1006.
M. Yuka, "Genetic analysis of ion channel disease-to explore the genetic background of complex pathologies," Journal of Clinical and Experimental Medicine, vol. 245, No. 9, Jun. 1, 2013; pp. 719-724.
W. Shimizu, "Arrhthmia as Ion Channel Disease-Gene Mutation and Gene Polymorphism," Journal of Clinical and Experimental Medicine, vol. 217, No. 6, May 6, 2006; pp. 631-635.
S. Akihito, "Diabetes and Genetic Abnormalities," Journal of Clinical and Experimental Medicine, vol. 207, No. 9, Nov. 29, 2003; pp. 625-629.
International Preliminary Report on Patentability directed to related International Patent Application No. PCT/US2015/036338, dated Jan. 3, 2017; 10 pages.

(Continued)

*Primary Examiner* — Mary K Zeman
(74) *Attorney, Agent, or Firm* — Sterne, Kessler, Goldstein & Fox P.L.L.C.

(57) ABSTRACT

Disclosed herein are system, method, and computer program product embodiments for building a community database of allele counts. An embodiment operates by receiving human variant datasets derived from samples generated by distinct users, wherein the users consented to share pooled variant observations with other users; determining that a plurality of variant observations meet the inclusion criteria for a pool; and calculating one or more anonymized allele statistics from the pool.

44 Claims, 23 Drawing Sheets

(56) References Cited

OTHER PUBLICATIONS

Office Action directed to related Japanese Patent Application No. 2017-521064, dated Mar. 18, 2020, with attached English-language translation; 6 pages.

Office Action directed to related Chinese Patent Application No, 201580041322.3, dated Apr. 3, 2020, with attached English-language translation; 17 pages.

* cited by examiner

Bibliography

Supporting | Excluded

Sort By: Date

Include in Results | Citation

☑ Ashkinadze et al. (2013) Combining fetal sonography with genetic and allele expression studies to secure a neonatal diagnosis of Bardet-Biedl syndrome. *Clin Genet* 83(6):553-9
  • Loss-of-function germline compound heterozygous mutant human BBS1 gene (c.1189-9C>G, c.1169T>G translating to p.M390R) is observed with childhood-onset recessive Bardet-Biedl syndrome in human (Northern European)

[Add a Note] [Exclude Paper]

☑ Charkoudian et al. (2013) Choroidal neovascularization in Bardet-Biedl syndrome. *Ophthalmic Genet* 34(1-2):52-4

☑ Cox et al. (2012) Phenotypic expression of Bardet-Biedl syndrome in patients homozygous for the common M390R mutation in the BBS1 gene. *Vision Res* 75:77-87

☐ Estrada-Cuzcano et al. (2012) BBS1 mutations in a wide spectrum of phenotypes ranging from nonsyndromic retinitis pigmentosa to Bardet-Biedl syndrome. *Arch Ophthalmol* 130(11):1425-32

☐ Daniels et al. (2012) Genotype-phenotype correlations in Bardet-Biedl syndrome. *Arch Ophthalmol* 130(7):901-7. doi: 10.1001/archophthalmol.2012.89

☐ Redin et al. (2012) Targeted high-throughput sequencing for diagnosis of genetically heterogeneous diseases: efficient mutation detection in Bardet-Biedl and Alström syndromes. *J Med Genet* 49(8):502-12

☐ Bennouna-Greene et al. (2011) Hippocampal dysgenesis and variable neuropsychiatric phenotypes in patients with Bardet-Biedl syndrome underline complex CNS impact of primary cilia. *Clin Genet* 80(6):523-31. doi: 10.1111/j.1399-0004.2011.01688.x. Epub 2011 May 25

☐ Billingsley et al. (2011) BBS mutational analysis: a strategic approach. *Ophthalmic Genet* 32(3):181-7. doi: 10.3109/13816810.2011.567319. Epub 2011 Apr 4

[Suggest Paper]

Drug Therapies

Diagnostic and Prognostic Papers

| Supporting | Excluded |

Sort By [Date ▼]

Include in Results | Citation

☑ ▸ U.S. Food and Drug Administration
  • Gilotrif [afatinib] has been approved as a treatment for metastatic non small cell lung cancer with EGFR exon 19 deletions.

[Add a Note] [Exclude Paper]

[Suggest Paper]

Edit Assessment

Phenotype: Bardet-Biedl syndrome

New assessment: Likely Pathogenic

Reportability: Reportable

Assessment note (viewable by your organization)

Beales et al. (2003) Genetic interaction of BBS1 mutations with alleles at other BBS loci can result in non-Mendelian Bardet-Biedl syndrome. Am J Hum Genet 72 (5):1187-99 shows evidence of non-Mendelian trait transmission.

(maximum 4000 characters)

Cancel

Previous notes danr@ingenuity.com Fri Apr 11, 2014 9:22 AM

METHODS AND SYSTEMS FOR INTERPRETATION AND REPORTING OF SEQUENCE-BASED GENETIC TESTS USING POOLED ALLELE STATISTICS

BACKGROUND

Efficient and accurate interpretation of DNA variants from sequence-based tests is a challenge for clinical laboratories. This challenge is compounded by increasing test complexity due to a greater number of genes assayed per test, emerging evidence for pathogenicity, and imprecise clinical phenotypes.

Generally, a sequence-based test workflow starts when a physician orders a sequence-based test for, as an example, a patient's cancerous tumor. The sequence-based test is used to better understand that tumor and which drugs might be most effective in treating the patient. After the test is ordered, samples are collected, sequence data are generated, and DNA sequence information is generated for that cancer sample. Then, informatics and analytics are applied to determine one or more variants. A variant is a DNA change that is present in that patient's sample relative to a reference, such as a reference genome. A clinical geneticist reviews the one or more variants. Sometimes, the observation of particular variants in the context of a particular sample may be referred to as a variant observations. In reviewing the variants, the geneticist assesses, for example, which variants are more likely to be the cause of one or more diseases or phenotypes of interest than others, which variants are pathogenic or likely pathogenic, and/or which variants are associated with modified drug response or drug toxicity. A report is then prepared based on the physician's order. For example, a lab director who is an expert in the field may sign out the test report, and the results will be sent back to the physician to help them better treat the patient.

This typical workflow suffers from several deficiencies. First, literature used to interpret the sequence results often needs to be procured and reviewed. To procure and review biomedical papers and other literature, for example, a geneticist or fellow will obtain and read the papers and interpret the different variants that are observed. However, the process between the time the test was ordered and the time the results get back to the physician can take a long time—time that could otherwise be spent treating the patient. In some instances, that time delay actually reduces the odds of successfully treating the patient's disease.

Second, there is a scalability challenge with the increasing number of sequence-based tests being ordered. It becomes more and more difficult to keep pace with test interpretation as test volumes increase. Further, as the number of tests increases, so does the number of variants and articles that are reviewed, thereby compounding the problem.

Third, the tests themselves are growing larger and more complex. Tests are changing from simpler tests that consider a handful of mutations in a gene, such as the BRCA1 or BRCA2 genes that predispose women to breast cancer, to tests that consider panels of dozens, hundreds or even thousands of genes. In some cases, labs are actually sequencing entire exomes all of the known exons of genes in a patient's genome—or even the entire genome of a patient. Such sequences have so much information in them that it results in a big data problem, where it becomes extremely challenging to interpret and pull out the relevant insights from the sequences.

Generally, entities interested in conducting clinical trials for studying variants spend a great deal of resources finding and enrolling patients for clinical trials. For example, a pharmaceutical company may be interested in studying patients having (or lacking) a particular genetic change or constellation of genetic changes, with the expectation that patients having (or lacking) those changes or variants may be expected to respond more favorably, or less favorably, to a particular therapy. The company enrolls several trial sites that test potential candidates for the genetic changes. Depending on the rarity of patients with the phenotype of interest who have (or lack) the desired variant or constellation of variants, many candidate patients may need to be tested to find a relatively small number of candidates that actually have (or lack) the desired variant or constellation of variants. There is even the possibility that enough candidates for the study are not identified to adequately power the trial.

In some cases, an article related to a variant has been published, but the publication is too recent to have been curated by the time a bibliography for a variant of interest is requested. The amount of time needed to curate an article can vary depending on the resources available for curation. For example, the time needed may be at least as long as necessary for a person to read through the article, and in many cases may be much longer. Nonetheless, the literature may contain relevant information on the particular variant of interest. If these papers are uncurated or partially curated prior to interpretation of a test, then patients may not benefit from valuable information that may be in them. In some instances, relevant information in non-curated content can be identified using textual searching techniques, such as natural language processing, or by construction of a "just-in-time" bibliography for one or more variants of interest. However, textual searching techniques on non-curated content often fail to provide results as relevant or as useful as those provided by curated content.

As for the information itself, the presence or absence of a single genomic variant is often not completely determinative of phenotypic effects. Yet only individual variants or individual DNA changes are generally being assessed, and often outside the context of the rest of the genome. For example, the ClinVar Database, run by the National Center for Biotechnology Information in the United States, provides information about the clinical significance of particular DNA changes. Yet, this mode of interpreting variants on a one-off basis, without appreciating the context of other genetic changes and modifier variants, is overly simplistic.

Another current issue in genetic testing interpretation occurs when a clinician interprets a genome for an individual's sequence-based test, and discovers a DNA change that looks extremely rare. The rarity of the change and the fact that it occurs in a gene that has been linked to a particular disease makes it compelling to conclude that the variant is causal for the rare disease phenotype affecting the patient. However, many sequencing studies that have been submitted to public domain can be extremely biased toward people of European descent. As a result, variants can be misclassified as being causal because of their scarcity in one population or ethnic group, even though they are less scarce in populations that have not had the same amount of sequencing investigation.

Generally, knowledge about particular genomic variants is continually being updated. The updates can come from clinical trials, research, regulatory approvals, experience treating patients, or other sources. However, the effect, impact, or occurrence of these updates is not always clear, even when they suggest a change to therapy or monitoring of a condition. Often, a patient may receive a diagnosis based on having a particular genomic variant, but is not made aware of subsequent developments in the understanding of the genomic variant.

BRIEF DESCRIPTION OF THE DRAWINGS

The accompanying drawings are incorporated herein and form a part of the specification.

FIG. 3 depicts an example bibliography, according to an embodiment.

FIG. 5 depicts an example treatment view, according to an embodiment.

FIGS. 9A and 9B depict example screenshots for including feedback provided by a user.

FIG. 19 depicts an example patient portal, according to an embodiment.

In the drawings, like reference numbers generally indicate identical or similar elements. Additionally, generally, the left-most digit(s) of a reference number identifies the drawing in which the reference number first appears.

DETAILED DESCRIPTION

Figure 1:
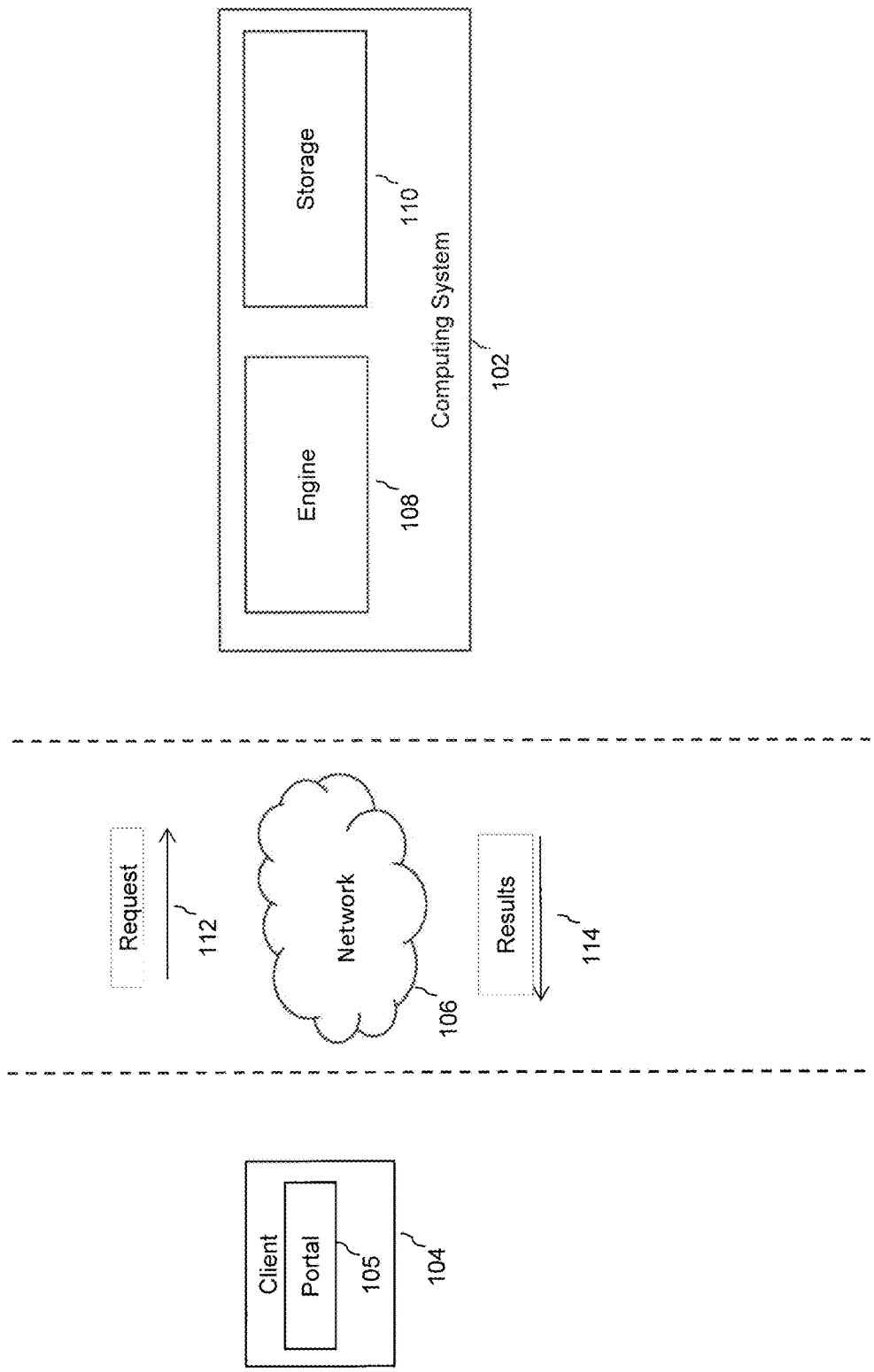
FIG. 1 is a block diagram of a system, according to an embodiment.

Provided herein are system, method and/or computer program product embodiments, and/or combinations and sub-combinations thereof, for assessing a genomic variant and for allowing one or more users to interact with a knowledge base.

Glossary

As used in the description that follows:

"Disease" means any phenotype or phenotypic trait of concern, including by way of example a disease or disease state, a predisposition or susceptibility to a disease, or an abnormal drug response. Illustrative and non-limiting examples of disease states include cancer, high cholesterol levels, congestive heart failure, hypertension, diabetes, glucose intolerance, depression, anxiety, infectious disease, toxic states, drug therapy side effects, inefficacy of drug therapy, alcoholism, addiction, trauma, etc.

"Therapy" and "therapeutic" include prophylaxis and prophylactic and encompass prevention as well as amelioration of symptoms associated with a disease state, inhibition or delay of progression of a disease state and treatment of a disease state.

"Protein" or "gene product" means a peptide, oligopeptide, polypeptide or protein, as translated or as may be modified subsequent to translation. A gene product can also be an RNA molecule.

"Literature" is the data that is used to build an information database. This data may come from public sources, such as databases and scientific and/or clinical publications, but it may also include proprietary data or a mix of proprietary and public data. In various embodiments, literature is derived from natural language (e.g., English language) formalized textual content. Articles, papers, and other references are all considered types of "literature."

"Variant" means any particular change in a nucleotide or nucleotide sequence relative to an established reference nucleotide or nucleotide sequence, including but not limited to single nucleotide variants, insertions, deletions, duplications and rearrangements. This also includes without limitation nucleic acid modifications such as methylation, as well as abnormal numbers of copies of the nucleotide or nucleotide sequence in the genome.

"Mutation" and "DNA change" each generally refer to a variant.

"Patient" generally means a biological organism with associated sequence information, which may include without limitation constitutional DNA sequence information from one or more patient tissues and/or sequence information from one or more patient tumors, and optionally phenotypic information.

"User" means a person who is using one or more methods and/or systems described herein to interact directly or indirectly with the knowledge base and/or one or more methods, systems, or devices described herein.

"Filtering" means annotating or altering one or more data sets. Filtering can mean keeping, adding, subtracting, or adding back data points from a data set. Filtering can mean masking one or more data points within the data set. Filtering can mean unmasking data points in a data set. In some embodiments filtering is an iterative process. In some embodiments filtering is performed with one or more filters. In some embodiments data points removed or masked by one filter are added back or unmasked by a second filter. In some embodiments filtering is performed on a list of variants. A filtered dataset can be smaller or larger than the original dataset. In some embodiments the filtered dataset comprises data points not removed from the original data set. In some embodiments a filtered dataset comprises more information than the original dataset. For example, a filtered dataset can comprise one or more of the following: the original data set, information regarding whether each data point is currently masked, information regarding whether each data point was previously masked, and information regarding previous filtering. The information regarding previous filters can be the kind of filter that was applied, any variables selected for the application of that filter, any assumptions made by the filter and or any information relied upon by the filter (e.g. information from a database).

Overview

A knowledge-based system and method intended to aid in the interpretation of variants observed in clinical sequencing data are presented. An embodiment of the present invention is HIPAA compliant and evaluates genomic variants in the context of deep, expert curation of the clinical literature and current gene and disease knowledge to provide a synthesis of published clinical cases, drug indications, and integrated guidelines such as NCCN (National Comprehensive Cancer Network), ASCO (American Society of Clinical Oncology), and ACMG (American College of Medical Genetics) incidental findings. In an embodiment, classification logic is provided to automatically suggest variant classifications based upon the standard ACMG guidelines or a user-defined scoring logic. This provides an evidence-based foundation for use by clinical geneticists, variant scientists and molecular pathologists for variant interpretation. Expert-curated content and analytic tools streamline and scale variant classification by incorporating phenotype information and up-to-date content into a scalable, reproducible, automated decision support workflow. An embodiment of the invention also enables efficient knowledge-based identification of patients (and/or sites having access to said patients) who would be ideally suited for enrollment in clinical trials in which patients are stratified, selected or enrolled preferentially based upon one or more genetic criteria.

Variants, such as DNA variants, are categorized based on curated content that is organized into structured information, leveraging an ontology in an embodiment. For example, variants may be observed in a sequenced-based test from a patient, annotated with relevant structured information from the knowledge base, and classified using a set of rules. Such curation can associate one or more variants directly with a disease or other phenotype. That is, analysis of structured content captured from the literature through curation can be used together with other information, such as allele frequency in a population of individuals unaffected by the phenotype of interest, to determine that the variant is very likely to be pathogenic or causal for a particular phenotype. On the other hand, consider a variant in a gene that has previously been found in individuals having a particular rare disease (for example, a disease occurring in fewer than one in 50,000 live births), but that is also present in 52% of all patients of European descent. It is extremely unlikely that a variant present in 52% of all Europeans is causal for a rare disease that is present in fewer than 1 in 50,000 live births. If the variant were causal for the particular recessive disease, and the variant is found in 52% of a particular population, the particular disease would be expected to be found in approximately 26% of the population. If the variant is highly unlikely to cause a disease, in one embodiment, that variant is categorized as benign. Particular methods, systems, or media of automated scoring or categorizing of variants are discussed in PCT Publ. No. WO 2013/070634 which is hereby incorporated herein by reference in its entirety.

An embodiment of the present invention summarizes relevant information for interpretation of a dataset based on that disease context. The system can allow a user to drill in on a particular variant (e.g., a BBS1 variant) and receive a dashboard of information that summarizes data related to this variant, its associated disease(s) or other phenotype(s), and its patient case context from the literature and various databases.

In an embodiment, the one or more users can include one or more curators. A curator is a user that reviews information from a knowledge base and organizes information therefrom. The one or more curators can include, for example and without limitation, a medical doctor, an individual with a degree in the relevant subject matter (e.g. Ph.D., M.S., B.S., etc.), an expert, or any combination thereof. The curators can work alone or in teams to review the pool of information from the literature to capture insights, facts, findings, etc., and organize them as structured information for incorporation into a knowledge base.

For example, the information may be structured according to an ontology using tools, such as the systems, methods, or media described in PCT Publ. No. WO 2013/070634, the contents of which are hereby incorporated herein by reference in its entirety. An ontology is a structured form of knowledge. An ontology can include relationships between genetic and phenotypic information By including information from the knowledge base in a structured form of the ontology, one can leverage the relationships between ontology elements to derive additional information.

The ontology can make it much easier to find relevant information. For example, if one queries the knowledge base with a concept, such as a disease or phenotype, the ontology understands from relationships in the ontology that the queried concept is related to or incorporates other concepts in the ontology. For example, searching the knowledge base for the concept of "breast cancer" leveraging an ontology may reveal related concepts of one or more genes related to breast cancer, or papers describing carcinoma of the breast or breast tumors or ductal carcinoma in situ. In this manner, even if the related concepts do not overlap directly in any way, the system understands the relationship between the concepts. If an article referred to breast cancer, and a user entered a query requesting mutations related to breast cancer, that user would receive the relevant results and insights not only from the article, but other articles identified as being related to the article because of links in the ontology. Although this is a simpler example, it illustrates the power of using the ontology to find and leverage related concepts.

As another example of how a knowledge base structured according to an ontology can make it much easier to find relevant information, a user can query using multiple attributes. For example, a user might be interested in a particular mutation in EGFR (epidermal growth factor receptor) and want to see all of the relevant literature evidence that discusses the relationship between that particular mutation and response to therapy by patients. Searching for articles using traditional key words and reading results that are returned is a typical way to find information. But due to limitations of key words and the researcher's time in absorbing an entire article to glean the relevant information, such a typical search is time-consuming and inefficient, and may not capture all the relevant information. Such a search and analysis is made much easier when using a knowledge base and ontology.

In an embodiment, one or more analyses are performed using information from the knowledge base. For example, information from the knowledge base can be used for translational applications of human DNA sequence interpretation, such as finding a DNA change that is causal for a human disease. Information from the knowledge base can also be used for clinical interpretation of sequence-based tests. Increasingly, tests are becoming available in labs that look at DNA changes or DNA variants. The results of such tests can help a physician to make a diagnosis of a disease, identify what drugs a patient's tumor might be susceptible to, identify what drugs might be best for treating a particular patient, etc. Conversely, the testing can indicate which drugs might not be effective in treating a particular patient based on the sequence information, e.g. the mutations that are present in a tumor.

Collecting, searching or analyzing patient-specific information in a knowledge base may require consent from that patient, and in one embodiment may be HIPAA-compliant. This patient consent can be acquired at various times and have a particular scope. For example, the patient may provide consent for any use or only a particular use of patient test information. Patient consent may be obtained at time of testing, sample extraction, or another time. For example, a patient consent form or questionnaire might ask, "Would you like to be informed in the future to the extent there are clinical trials that may benefit you based on your test information?" Such a question can be included, for example, as a checkbox in an electronic questionnaire. If the patient consents, then the patient's test information may be used for clinical trial matching. For example, the patient's genetic test information may be compared to with drug trials being run by pharmaceutical companies, to see whether the patient is an appropriate match for a trial. To drug companies, the genetic information can be very useful for predicting which patients will or will not likely respond to a drug. Moreover, patients that actually have those genetic changes in which a pharmaceutical company is interested would benefit from knowing that such a drug is coming up, and that they might qualify for treatment in the context of the trial, especially if their current therapy has been unsuccessful. So, a patient may have quite an interest in providing consent to usage of the patient's test information for clinical trial matching.

The benefits of obtaining this advance consent are significant. As discussed herein, it can be incredibly difficult to find patients with particular genomic variants or constellations of variants by randomly sampling individuals in a population during a study. Maintaining a database of patients harboring genomic variants that have already been seen results in a valuable catalog of people, so that trials and trial sites could be enrolled more quickly, benefits patients by providing more rapid access to targeted therapies, and benefits pharmaceutical firms by helping them get new treatments to market more rapidly.

Portal

FIG. 1 is a block diagram of a system 100 by which a user can interact with a knowledge base over the cloud. Such a system allows users from disparate locations to make use of a common set of data and contribute their own information to the knowledge base.

System 100 includes a computing system 102 that communicates with client 104 over network 106. Computing system 102 may have server functionality. Computing system 102 includes engine 108 and storage 110. Engine 108 can be configured to perform processes, such as any of the processes discussed herein. Storage 110 can store data, such as information received from computing system 102. Storage 110 can include a database, a knowledge base, any form of computer storage, or any combination thereof.

Client 104 may be any type of computing device, such as and without limitation, a personal computer, a mobile phone, a tablet, a PDA, a workstation, an embedded system, a game console, a television, a set top box, or any other computing device. In an embodiment, A user may operate an interface or portal 105 on client 104 to access information located on computing system 102. Portal 105 may be a native application that is specific to a particular computing device platform run by client 104. Alternatively, portal 105 may be accessed via a browser, such as a web browser, running on client 104.

Network 106 may be any network or combination of networks that can carry data communications. Such a network 106 may include, but is not limited to, a local area network, metropolitan area network, and/or wide area network, such as the Internet.

In an embodiment, computing system 102 receives request 112 from client 104. Request 112 can include, for example and without limitation, a request for a report, test, test results, or any combination thereof. Computing system 102 can process request 112 to produce results 114 based on information stored in storage 110. Computing system 102 can then transmit results 114 to client 104.

Figure 2:
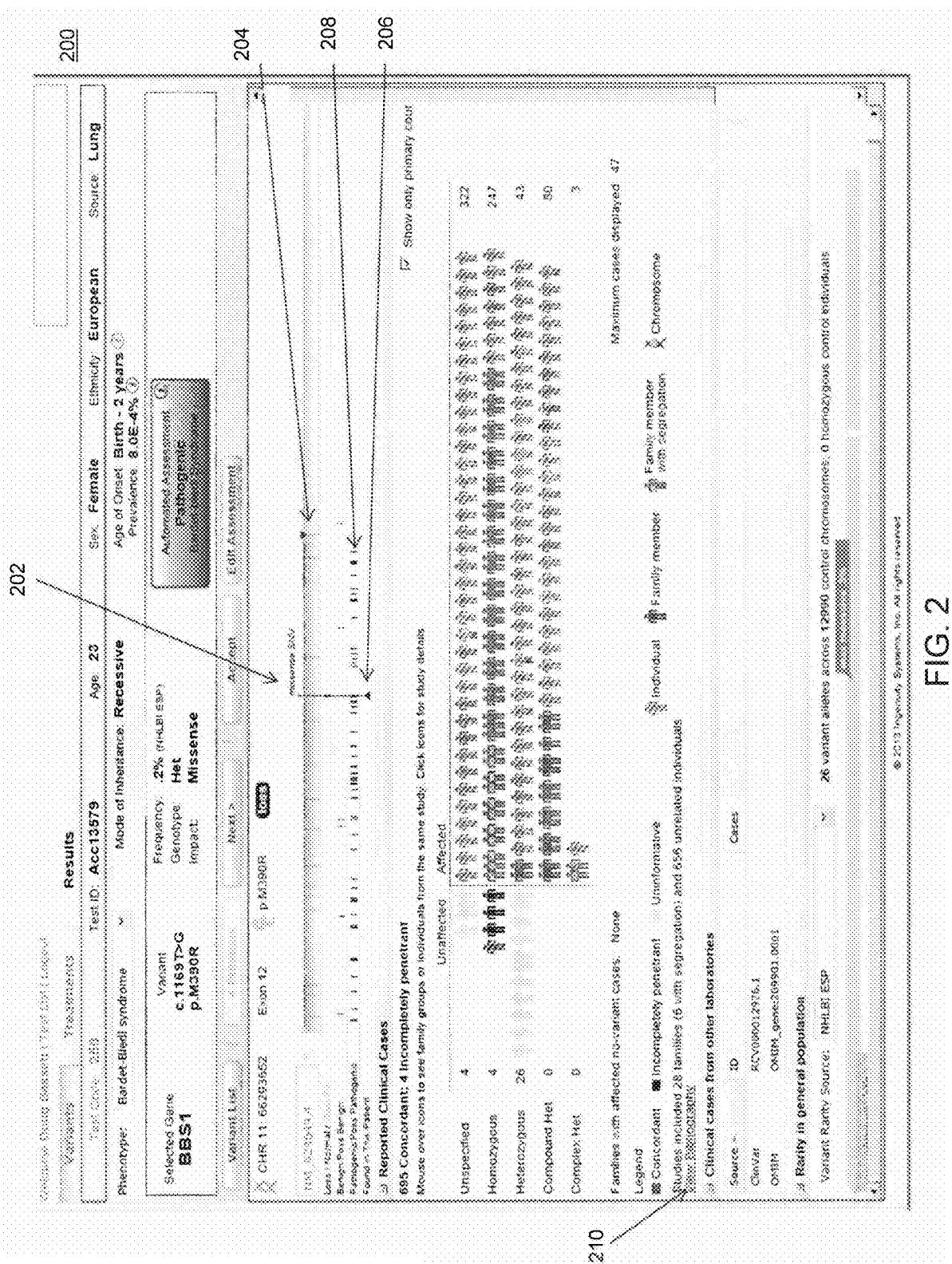
FIG. 2 depicts an example dashboard, according to an embodiment.

FIG. 2 depicts an example dashboard 200, according to an example embodiment. In an embodiment, information in dashboard 200 is provided by computing system 102 to client 104 for display via portal 105. Dashboard 200 provides information about whether a particular genomic variant is relevant to a particular phenotype. In this example, the gene is BBS1 (Bardet-Beidl Syndrome 1), the variant is c.1169T>G, and the phenotype is Bardet-Beidl syndrome. This gene, variant, and phenotype combination is used only for illustrating an example. One of skill in the art would recognize that the dashboard may include any combination of other genes, variants, and phenotypes without departing from the spirit and scope of the present invention.

In dashboard 200, the location of the genomic variant in the context of the gene is shown at location 202. As shown in row 204, this gene (BBS1) has multiple exons. Indicator 206 identifies the location of the DNA mutation within the gene. Row 208 shows where else in the gene damaging mutations have been identified based on information located in the knowledge base. This display gives a user a quick view to see whether this variant sits in a hot spot of other DNA changes that can cause the disease.

The "Reported Clinical Cases" section of dashboard 200 provides a synthesis of clinical cases related to the variant that are located in the knowledge base. This may include, for example, of all the variant-specific patient cases in the biomedical literature related to this phenotype that are stored in the knowledge base of computing device 102. From this synthesis, a user can quickly see groups of patients who have both the phenotype of interest and genes having this variant. One can also quickly see patients who had this particular variant but did not manifest the phenotype. Such patients are highlighted in the interface of dashboard 200. Patients who have this genomic variant but who do not manifest the phenotype could be of interest to determine whether this variant is not causally related to the phenotype, and/or to determine whether there is a combination of variants that suppress the phenotype even when this particular variant is present. One can very quickly access a bibliography via a link 210 to the references and the literature related to this variant. In an embodiment, such links are embedded in the icons shown as part of the reported clinical cases.

FIG. 3 depicts an example bibliography interface 300, according to an embodiment. In an embodiment, bibliography interface 300 is provided by computing system 102 when a user selects link 210 in dashboard 200. Bibliography interface 300 shows whether there are publications related to genetic interactions between disease and the variant of interest. From bibliography interface 300, a user, such as a lab director or geneticist, can quickly assess the literature evidence related to this variant and this phenotype. The user can select specific articles to include on a report back to the physician. Bibliography interface 300 may separate relevant literature into multiple tabs. For example, literature supporting the analysis shown on dashboard 200 may be provided in one tab, while literature, excluded from analysis is provided in another tab. Literature may be excluded from analysis if it is identified as, for example, untrustworthy or not actually relevant to the variant or phenotype of interest. As the user is reviewing the bibliography, the user may add a note for a particular result, or may request that a particular result be excluded from the list of relevant documents.

Figure 4:
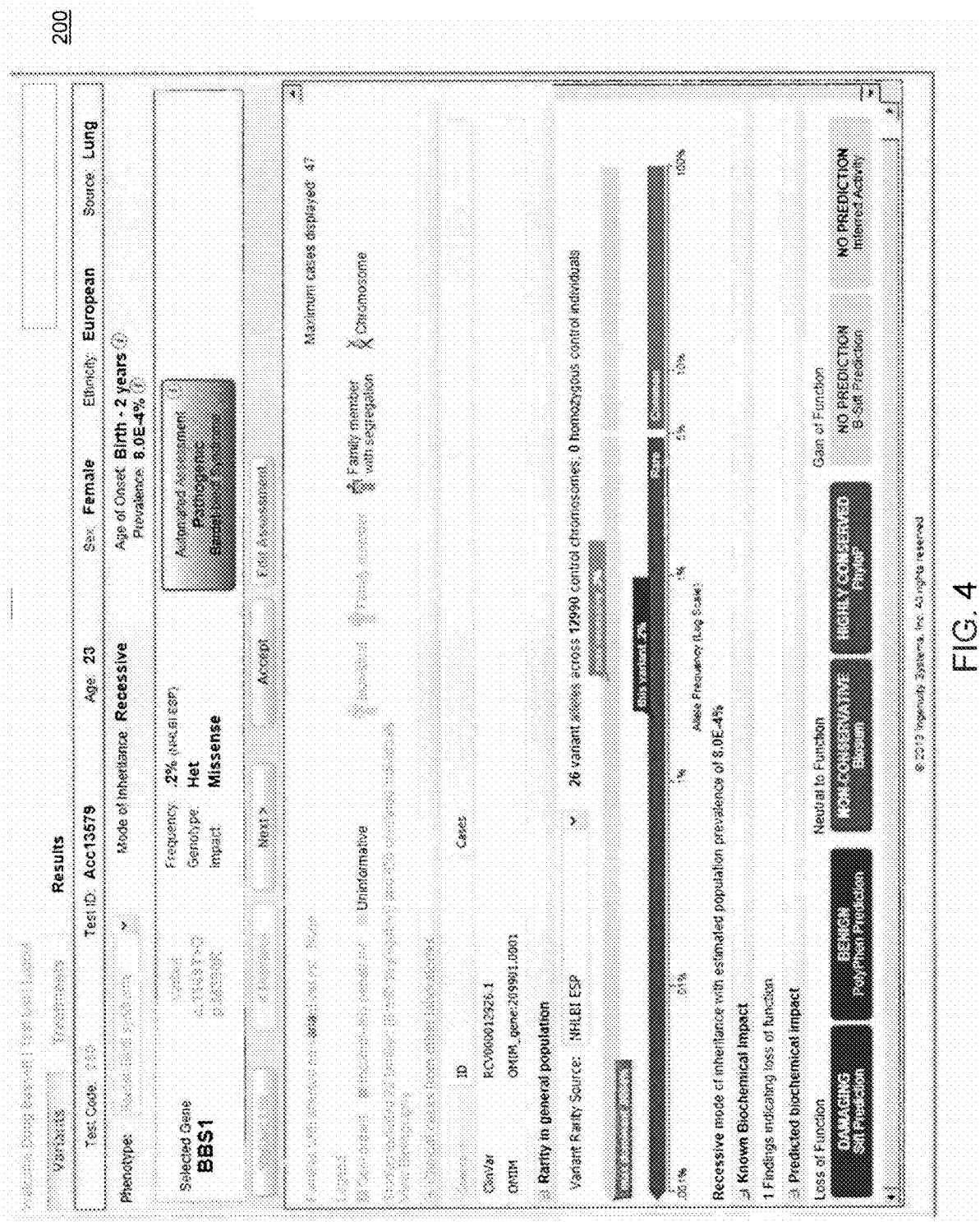
FIG. 4 further depicts the example dashboard, according to an embodiment.

FIG. 4 depicts further information provided by dashboard 200, according to an example embodiment. For example, dashboard 200 can also provide clinical case evidence that was observed in other laboratories, shown in dashboard 200 under the heading "Clinical cases from other laboratories." In the example of FIG. 4, there is a database called "ClinVar" that contains assessments from other labs. This may be a useful reassurance to a user. In the example of FIG. 4, if a lab planned to sign out a test saying that the BBS1 variant was pathogenic for this patient, they can be reassured that one or more other labs classified this variant as pathogenic. Information from other laboratories may be obtained by computing device 102 by, for example, consulting a repository of information from such laboratories, and/or by direct links between computing device 102 and those laboratories.

Dashboard 200 also provides an assessment of the rarity of this variant in the general population. As discussed above, if a variant is common in a given population, then it is unlikely that the variant is causal of a rare disease. On the other hand, if a variant is rare in a given population, then it is consistent with that variant being causal for a rare disease. In the example illustrated in FIG. 4, the rarity percentage illustrated shows that that this variant's prevalence in the population is consistent with the expression of the disease (phenotype) in the general population. This strengthens a finding that the variant (BBS1) is causally related to the disease (Bardet-Beidl Syndrome), because it is observed at a frequency within the range expected for the disease.

In an embodiment, dashboard 200 can provide an assessment of the biochemical impact of the DNA change due to the variant. Dashboard 200 can provide one or more links to articles where a user, e.g. a scientist, can explore the biochemical impact of this particular DNA protein change, and also predict biochemical impact. For example, various tools can predict whether a given DNA change is damaging or likely to not be damaging to a protein's function. Such tools may include, for example and without limitation, the SIFT (Sorting Intolerant from Tolerant) algorithm; the PolyPhen (Polymorphism Phenotyping) algorithm; the Blosum matrix; the PhyloP model; and the B-SIFT (Bi-directional SIFT) algorithm. Example criteria for these tools can include whether a given DNA or protein change is a conservative or non-conservative amino acid substitution, whether a variant is observed at a highly conserved region across mammals even if the effect of the variant is not known. That a particular variant impacts a nucleotide or protein location that is highly conserved across all mammalian species could suggest that the variant is doing something important. This information and these algorithms can be used to predict whether this DNA change is likely to perturb a gene or protein function or, alternatively, enhance or augment function or create a new function in some way, for example through gene fusion.

FIG. 5 depicts an example treatment view 500 that includes a synopsis of drugs and/or therapies that could be relevant to a patient having a particular genomic variant or constellation of variants. View 500 may be accessed via a link from dashboard 200 (not shown). In the example of FIG. 5, treatment view 500 depicts a drug treatment identified in the knowledge base as related to lung cancer caused by a particular genetic mutation (EGFR exon 19 deletion). In this example, evidence has been curated from the FDA's website and the prescribing information indicates that this treatment is relevant for patients who have a tumor, specifically a cancer having exon 19 deletion in the EGFR. If a user selects the link, the user will be directed to the underlying reference or data source. For example, if a user selects the "U.S. Food and Drug Administration" link shown in FIG. 5, the user will be taken through to the FDA's website to see the prescribing information for this drug, from which the data were curated.

In an embodiment, treatment view 500 may also depict clinical trials that are in progress. For example, a pharmaceutical company may be conducting a trial that is looking for patients having certain mutations in the context of a certain disease, because they are testing a new therapy that could help these patients. When viewed by a physician or researcher with knowledge of specific patient information (or if patient information is included in the knowledge base), identification of such clinical trials in the treatment view could enable a prospective enrollee to be put in contact with the relevant company (via a physician, a laboratory, or directly) about enrolling in the clinical trial. If a prospective enrollee has exhausted other therapeutic options, this listing could also inform the patient of a late-breaking development that may benefit the patient.

Enhanced Pre-Profiling

Figure 6:
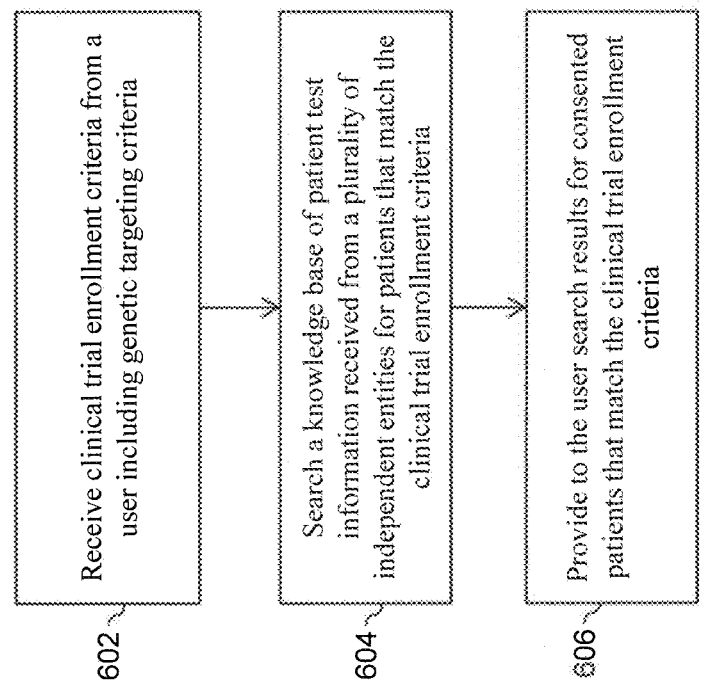
FIG. 6 is a flowchart for determining a clinical trial candidate, according to an embodiment.

As more and more patient test information is collected in the knowledge base, the knowledge base can be used for more than just extracting relevant information from literature and clinical trials. In an embodiment, the wealth of patient genetic information included in the knowledge base can be used, if authorized by the patients, to identify candidates for available clinical trials. Data from multiple sites and organizations can be combined in a knowledge base and searched to identify sites and patients that qualify for a particular targeted clinical trial, such that those sites and/or patients could be enrolled in the trial more rapidly. This could streamline and accelerate enrollment of trials, enabling patients to gain more rapid access to life-giving therapies that are more likely to be effective in treating their disease, while also enabling pharmaceutical companies to bring new therapies to market faster and at significantly reduced cost relative to conventional methods. FIG. 6 is a flowchart of a method 600 for determining a candidate for a clinical trial, according, to an embodiment. Method 600 can be performed by processing logic including hardware (e.g., circuitry, dedicated logic, programmable logic, microcode, etc.), software (e.g., instructions run on a processing device), or a combination thereof. In an embodiment, method 600 is performed by computing system 102.

In block 602, clinical trial enrollment criteria is received from a user. In an embodiment, computing system 102 receives the clinical trial enrollment criteria from the user via portal 105 on client 104. The clinical trial enrollment criteria can include genetic targeting criteria, patient test information parameters, patient sequence variant parameters, patient phenotype parameters, patient consent parameters, and the like.

In block 604, a knowledge base of patient test information is searched for patients (and/or sites with access to patients) that match the clinical trial enrollment criteria. In an embodiment, computing system 102 searches a knowledge base located in storage 110 for such patients. For example, the knowledge base can be searched for trial candidates having a particular constellation of variants for which a drug or therapy is very likely to respond.

In an embodiment, the searching includes accessing at least one of a patient electronic medical record or a derivative of a patient electronic medical record. Computing device 102 may connect with an electronic medical records provider or database over a network, such as network 106, so as to gain access to patient information.

In an embodiment, the patient test information is located in a knowledge base in storage 110. For example, patient test information may be received by computing device 102 from a plurality of independent customer entities via a network, such as network 106. For example, multiple testing sites can collect test information for patients (such as when they are tested and the results of that test), regardless of whether the testing is for a particular clinical trial of interest or not. At any point during the process, such as prior to testing, the patients can provide consent to allow subsequent uses of the test information, such as to determine whether the patient could be a candidate for a clinical trial. Such patient test information and consent may be stored by computer 102 in storage 110. That patient test information and/or consent may then be compared to the received patient test information parameters and/or the received patient consent parameters to see whether the patient is a match for the clinical trial.

In an embodiment, patient phenotype information is located on computer system 102, and is structured and searchable according to an ontology. For example, a knowledge base can include information that relates patient phenotype information to one or more variants, such as those discoverable by sequence-based testing. When patient phenotype information is received by computing device 102, computing device 102 may process the information using engine 108, and store the information in an ontological knowledge base located in storage 110. That patient phenotype and genotype information may then be compared to the received desirable patient clinical trial parameters, including desirable genotypic information, to see whether the patient is a match for the clinical trial.

In block 606, search results for consented patients that match the clinical trial enrollment criteria is provided to the user (e.g., laboratory or company searching for clinical trial participants) by, for example, computing system 102. The search results can include any combination of information about the patient, e.g. demographic information, patient phenotypes, genomic variants, or any other information useful for matching or excluding a patient from a clinical trial. Additionally or alternatively, the search results can be aggregated by site. For example, the search results may list the top five sites that have consented patients meeting the enrollment criteria and/or the number of patients at each site that match the clinical trial enrollment criteria.

Figure 19:
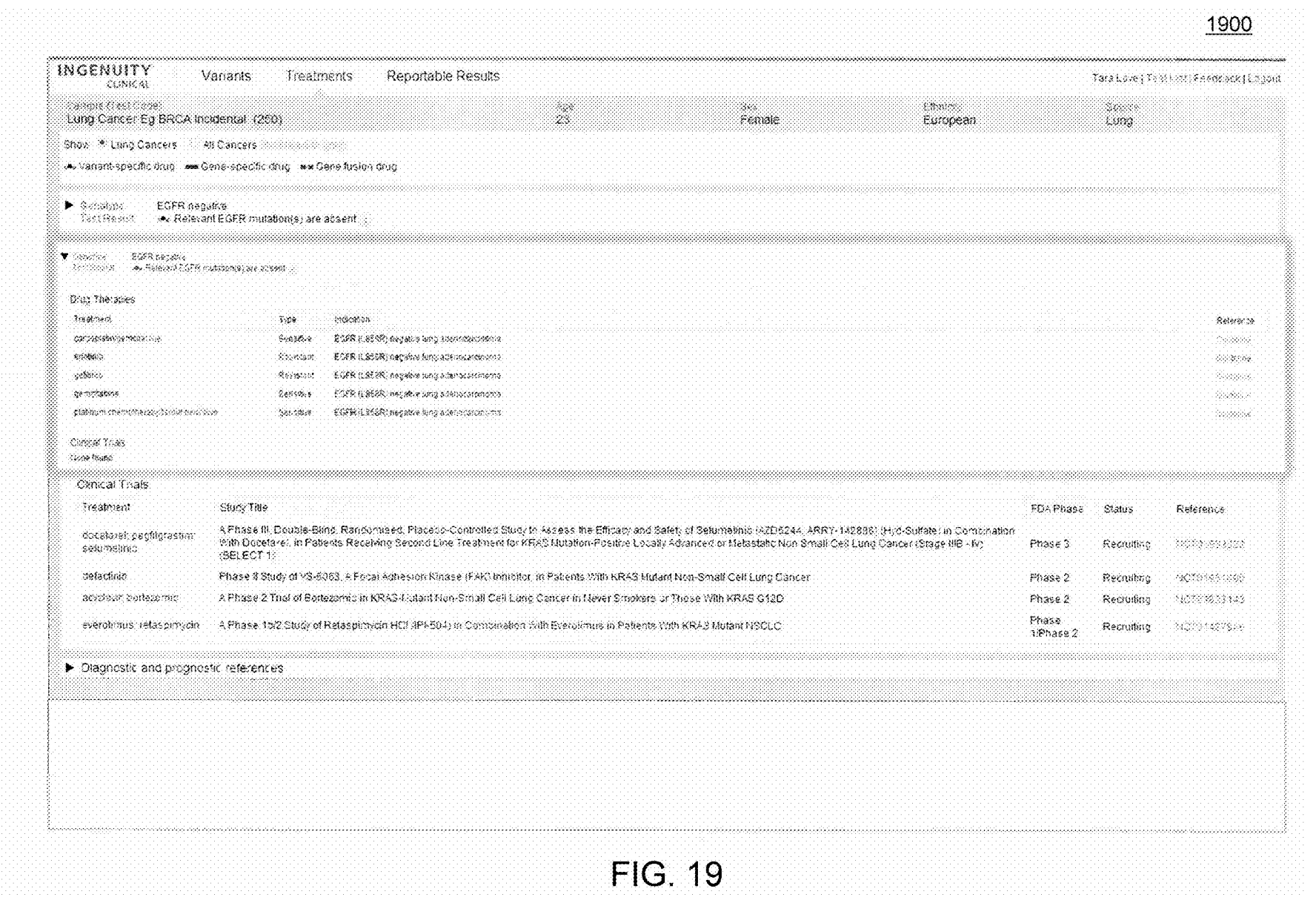

In an embodiment, a patient portal that enables one or more patients to view test information is provided. For example, a patient may access computing system 102 via portal 105 running on client 104. One of skill in the art will recognize that portal 105 may have different capabilities depending on whether it is intended to be used by a laboratory/researcher or whether it is intended to be used by a patient. The patient portal can be accessed by individuals or entities authorized by the patient, such as the patient, the patient's family, a care provider (e.g. a physician or geneticist), a researcher, an insurer, or any combination thereof. Further details regarding a patient portal are described below with respect to FIGS. 18 and 19. Although FIG. 19 illustrates an example patient portal, embodiments support any patient portal that enables one or more patients to view test information.

In an embodiment, various data can be obtained based on a patient's interactions with the patient portal. Such data can include, for example and without limitation, whether the patient is likely to still be alive (based on the patient's consistent or continued interaction with the system), the patient's geographic location, the patient's interest in a clinical trial, or additional patient phenotype information. For example, when a patient logs into the patient portal, this can indicate that the patient is alive, still has a condition for which treatment is sought, and is interested in receiving information about other therapy or treatment options. Similarly, if a patient is inputting (or a provider is inputting on their behalf) new test information or phenotype information, it can indicate whether or not a patient is affected by the relevant phenotypes. Also, patients or their providers may input health record information that may assist in assessing whether patients may be well-suited for a particular clinical trial, for example what treatment regimens the patient has been exposed to, for what length of time the patient has been diagnosed with a particular phenotype, and whether the phenotype is considered successfully treated or not.

In an embodiment, one or more patients that match the clinical trial enrollment criteria are enrolled into the clinical trial. In an embodiment, one or more sites or independent organizations that have access to patients are selected for activation/enrollment in a trial based on the fact that they have already seen a significant number of patients with desirable trial characteristics, including but not limited to desirable genotypic characteristics which make them well-suited for the trial. In one embodiment, patients are excluded based on the fact that they have test information, including genotypic characteristics, that make them unsuitable for a particular clinical trial.

Facilitating genotypic assessment of patients to identify patients and/or sites of interest for one or more trials resolves several issues traditionally involved in conducting clinical studies, and can reduce many of the expenses and risks associated with finding potential candidate patients to enroll. Having access to genetic information about potential candidates can eliminate, or at least reduce, the situation in which a study provider has to wait for individuals to respond to advertisements or referrals about the clinical trial. Plus, traditionally, there is no assurance that the individuals responding to such advertisements or referrals actually have the specific variant to be studied. Additionally, searching a knowledge base of patients test information compiled from multiple organizations as discussed here reduces the risk, time delay and cost of testing large numbers of people, only to find that enough people with the genomic variant of interest have not been identified.

Bibliography

Figure 7:
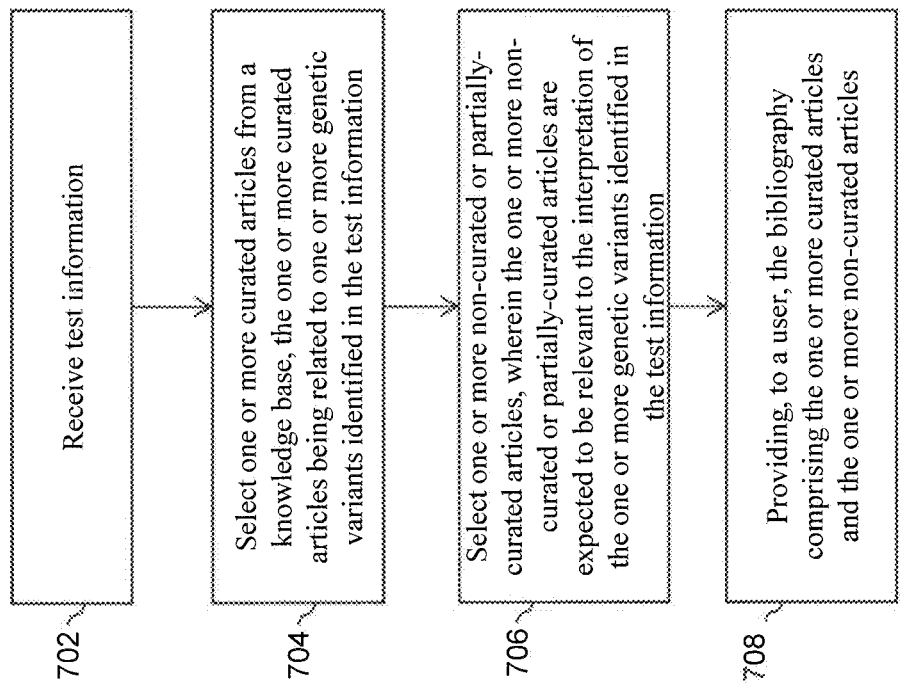
FIG. 7 is a flowchart for providing a bibliography, according to an embodiment.

To maximize usefulness and relevance, the bibliography of references associated with a given variant can be updated on a routine basis to ensure that the most recent knowledge about the variant is included in a user's result set. The bibliography of references may also be updated by the system upon request, upon receipt of test information relevant to certain biomedical literature, or in anticipation of receipt of test information relevant to certain biomedical literature. In an embodiment, the bibliography is generated in real time when a user requests the bibliography from dashboard 200. This type of "just-in-time" bibliography is useful to capture as much relevant information as possible, without missing the most recent information simply because it is uncurated or only partially-curated. In another embodiment, the bibliography is updated in real time when test information containing one or more variants is uploaded into the system. FIG. 7 is a flowchart for a method 700 for providing a bibliography, according to an embodiment. Method 700 can be performed by processing logic that includes hardware (e.g., circuitry, dedicated logic, programmable logic, microcode, etc.), software (e.g., instructions run on a processing device), or a combination thereof. In an embodiment, method 700 is performed by computing system 102.

The bibliography, such as bibliography 500, can include both curated and non-curated or partially-curated content. Partially-curated content may refer to content that has undergone some curation, but that has not been completely curated. Partially-curated content may be included in the knowledge base, even though it does not include the level of detail of curated content. In one non-limiting example, partially curated content could include articles that have been validated to relate to a particular variant and a particular disease phenotype. In another non-limiting example, partially curated content has been classified as to whether the paper contains functional evidence and/or clinical case evidence. This allows the user to be provided with more relevant article evidence, not only articles that have been curated in the biomedical literature as being related to one or more variants observed in the patient's test information, but also additional articles or references from the knowledge base or literature base that have not yet been curated or that have been partially-curated but that are expected to be relevant to the variant based on, for example, keywords within the reference.

In block 702, test information is received. In an embodiment, computing system 102 receives the test information. Test information can be received from one or more sources. For example and without limitation, test information can be received from a test subject, a laboratory, a care provider, an insurer, and the like.

In an embodiment, the test information is received via an automatic pipeline. The automatic pipeline can include a process for automatically receiving, queuing, or acting on test information. For example, the test information may be obtained automatically from a genetic database, publications database, customer instrument, or other source. As discussed herein, for example, the test information can be incorporated into the knowledge base, subjected to one or more analyses, included in a bibliography, etc.

In block 704, one or more curated articles are selected from a knowledge base. In an embodiment, computing system 102 selects the one or more curated articles from the knowledge base. The one or more curated articles can be relevant to one or more genomic variants identified by the test information. For example, curated articles related to the BBS1 gene may be selected. In another example, such as that shown in FIG. 5, curated articles related to EGFR exon 19 deletions may be selected.

In an embodiment, the one or more curated articles are organized in the knowledge base according to an ontology. The knowledge base can be queried using the features of the ontology to find one or more articles relevant to the one or more genomic variants.

In block 706, one or more non-curated or partially-curated articles are selected. In an embodiment, computing system 102 selects the one or more non-curated or partially-curated articles. The one or more non-curated or partially-curated articles can be expected to be relevant to the interpretation of the one or more genomic variants identified in the test information.

In an embodiment, selecting one or more non-curated or partially-curated articles from the knowledge base includes determining that the one or more non-curated or partially-curated articles refers to a gene identifier corresponding to the one or more genomic variants, and a protein or a nucleic acid identifier for the one or more genomic variants. For example, non-curated or partially-curated articles containing a mention of one or more specific variants in the BBS1 gene, which makes it appear that the article concerns this particular DNA or protein change, can be selected.

In an embodiment, selecting one or more non-curated or partially-curated articles includes determining that the one or more non-curated or partially-curated articles corresponds to the one or more genomic variants using natural language processing. In one embodiment, the natural language processing is performed leveraging a biomedical ontology.

In block 708, the bibliography is provided to a user. In an embodiment, computing system 102 provides the bibliography to the user. The bibliography can include the one or more curated articles and the one or more non-curated articles. In this manner, the "just-in-time" bibliography includes not only the papers that have been curated, but also late breaking, interesting information having text in it that suggests relevance the information is relevant to interpretation of the variant of interest.

Receiving both curated and non-curated or partially-curated content can be very useful for interpreting a particular patient's test information. Although curated content may be considered more relevant or reliable due to the fact that it has been curated, there is a time lag between when information becomes available and when that information is mated. Analysts would still be interested in receiving information that has been published so recently that it has not yet been able to be curated, if that information is determined to be reasonably relevant to the test information. For example, if an article just came out yesterday that relates to a patient's test, the physician and the laboratory would want to know about that article. The physician and laboratory might not care whether a reasonable amount of time has passed for the article to be completely curated; instead, they would want to see any potentially relevant, late-breaking information, and make the determination as to whether or not the information is relevant to treatment of that patient.

In an embodiment, feedback from one or more users is received about the articles presented in the bibliography. Because the users may be reading the articles and signing patient test reports, the one or more users can provide meaningful information about the articles. For example, users can specify how related an article in the bibliography is to the variant of interest. For example, a user could pull up the bibliography and indicate that a paper is nominally related to the particular variant or the particular phenotype, that the paper does not meet the quality standards, or that the paper has sufficient information to indicate that the variant is causal for a particular phenotype. The user can indicate this, for example, by selecting to include or exclude this paper from a report or include or exclude it from the analysis in an automated assessment of a variant. The user may also suggest additional papers that may be relevant to one or more variants that may not be displayed in a bibliography. In one embodiment, these articles are prioritized for curation and/or included in the bibliography for said one or more variants in the future for said user or other users who are interested in said one or more variants.

Crowdsourcing Variant Assessment

Figure 8:
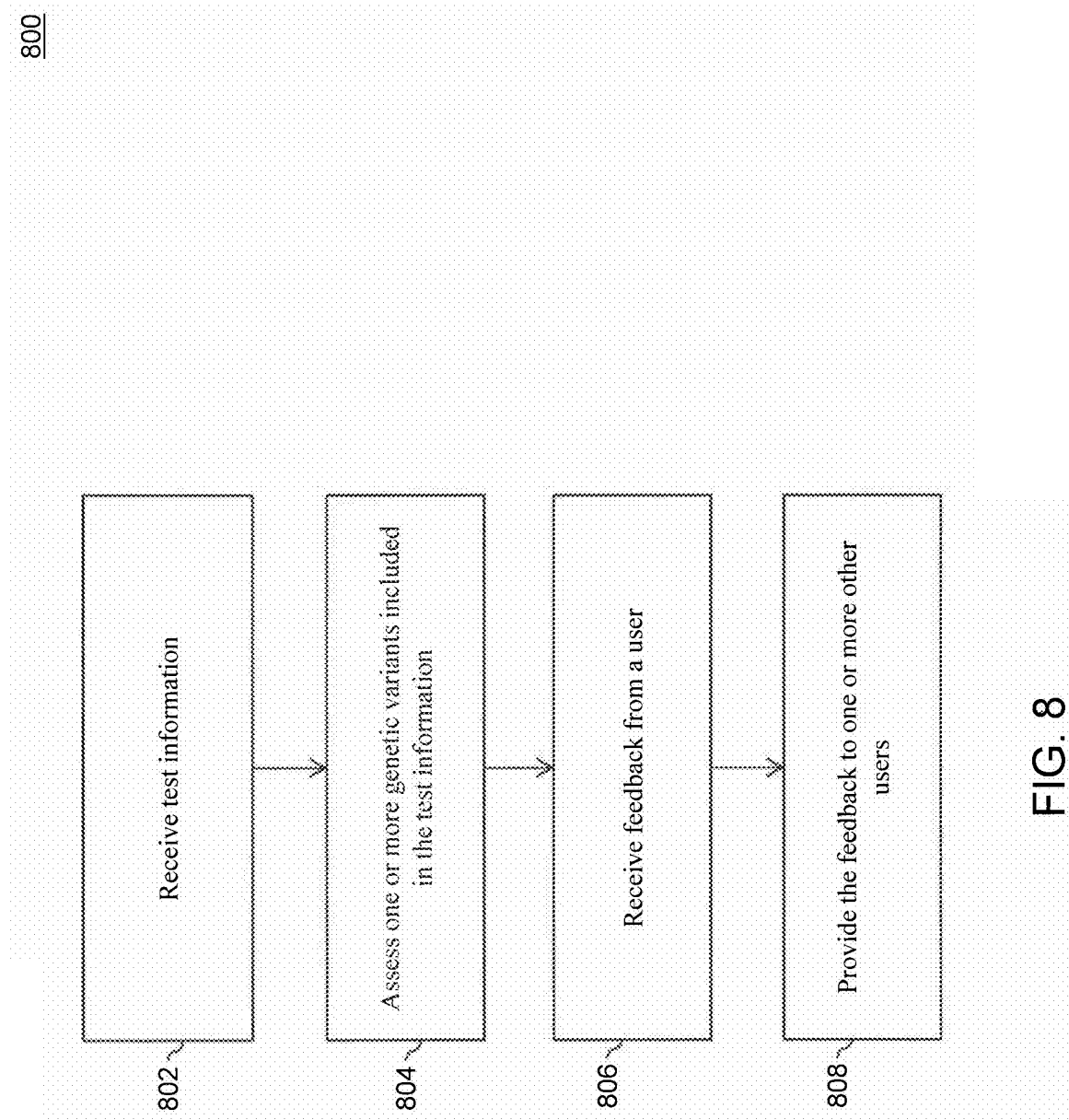
FIG. 8 is a flowchart for crowdsourcing variant assessment, according to an embodiment.

In an embodiment, the data in the knowledge base is static, in that a user cannot change or challenge the information. Many times, though, a user (such as a physician or laboratory researcher) is in a good position to evaluate the knowledge base data, since the user is presumably accessing and analyzing the data in the context of a present interest. Accordingly, in another embodiment, the data in the knowledge base may be enhanced by allowing users to edit or annotate the data, either actively or passively (that is, as a natural part of their workflow). Such collection of data from users over the network is referred to herein as crowdsourcing. FIG. 8 is a flowchart of a method 800 for crowdsourcing variant assessment, according to an embodiment. Method 800 can be performed by processing logic that includes hardware (e.g., circuitry, dedicated logic, programmable logic, microcode, etc.), software (e.g., instructions run on a processing device), or a combination thereof. In an embodiment, method 800 is performed by computing system 102.

In block 802, test information is received from the user. In an embodiment, computing system 102 receives the test information.

In block 804, one or more genomic variants included in the test information are assessed. In an embodiment, computing system 102 assesses the one or more genomic variants. The one or more genomic variants can be assessed using any combination of assessment methodologies, such as those discussed herein or by PCT Appl. Publ. No. WO 2013/070634, the contents of which are hereby incorporated herein by reference.

In an embodiment, the assessing includes classifying the one or more genomic variants into a clinical significance category. The one or more genomic variants can be classified using a variant scoring logic. Examples of clinical significance categories include, but are not limited to, pathogenic, likely pathogenic, uncertain significance, likely benign, and benign.

In block 806, feedback is received from a user. In an embodiment, computing system 102 receives the feedback on the assessment from the user. The feedback may be received as input from the user interacting with a portal web page, native application, or other input source. The feedback can be received in various ways. For example, in an embodiment, receiving feedback includes receiving a selection of one or more assessed genomic variants, and receiving a classification of the one or more selected variants. In another embodiment, receiving feedback includes receiving an indication of the value or relevance of a reference for the assessment of the one or more variants. For example, the feedback may be provided in the form of a "thumbs-down" or "thumbs-up" button. In another example, the feedback can include whether a reference was included or excluded by a user from a report. In yet another embodiment, receiving feedback includes receiving an indication of a non-curated or incompletely curated article and prioritizing curation of the non-curated or incompletely curated article. In a further embodiment, receiving feedback includes receiving curation of a non-curated or incompletely curated article from the user. In a further embodiment, receiving feedback is passive, for example, one or more users manually suggest a clinical classification for one or more variants that is different from a machine-predicted classification generated by a decision support system. This could trigger an evaluation and/or curation of evidence related to the variants or review and potentially adjustment of the machine-predicted support scoring logic to improve future predictive power of the decision support system. The curation can include phenotypic information of the variant, in which the phenotypic information is structured according to an ontology. In any embodiment, the feedback can indicate that the non-curated or incompletely curated article is relevant for assessing one or more genomic variants included in the test information.

In an embodiment, the test information comprises phenotypic information of the variant structured according to an ontology.

In an embodiment, the feedback provided by the user is used in subsequent assessments of the one or more genomic variants. This feedback is training for computerized systems by humans that are skilled in the art of variant interpretation, and can be used to continually improve the assessments over time (e.g., as in machine learning). That is, the assessments improve as more people score and assess the variants, because the training makes the predictive algorithms and the content stronger.

In block 808, the feedback is provided to one or more other users. In an embodiment, computing system 102 provides the feedback to one or more other users.

Using a bibliography feature, one user can see articles that are related to the one or more variants and drill in on them to obtain more information. The user can also suggest including another reference in the bibliography, such the user's favorite reference for assessing the variant. When the next user accesses the bibliography associated with the same variant, that next user can add information about that reference and select that reference for the user's report. These iterative efforts can improve both the quantity and quality of references available to users.

In an embodiment, a second user is provided with the feedback of the first user regarding the one or more genomic variants. For example, computing system 102 can receive second test information from a second user, in which the second test information includes the one or more genomic variants. When providing an assessment of the second test information to the second user, the computing system 102 can also provide the feedback from the first user.

Figure 9A:

FIGS. 9A and 9B depict example screenshots 900 and 950 that illustrate feedback provided by a user entered into a bibliography. Screenshot 900 includes clinical cases from other laboratories, rarity of the genetic variant in the general population, references of known biochemical impact, and predicted biochemical impact. The rarity of the variant in the general population may be displayed for one or more sources, which can be selected using dropdown 902.

The internal lab variant classifications and annotations databases may be integrated into a private instance used by the tool. Then, one or more users can annotate the private instances of the classifications or annotations. Screenshot 950 includes a number of fields for editing an assessment, for example an assessment provided in screenshot 900. In screenshot 950, a user may view or edit a phenotype, an assessment, a reportability, a note, and previous notes for an assessment. The reportability may refer to whether the edits are reportable or not reportable.

Although FIGS. 9A and 9B provide example screenshots 900 and 950, embodiments of the invention support other types or arrangements screens for viewing or editing user feedback, in which any information related to the user feedback can be presented to a patient or other user, including but not limited to any of the information discussed herein.

Multi-Variant Classification

Figure 10:
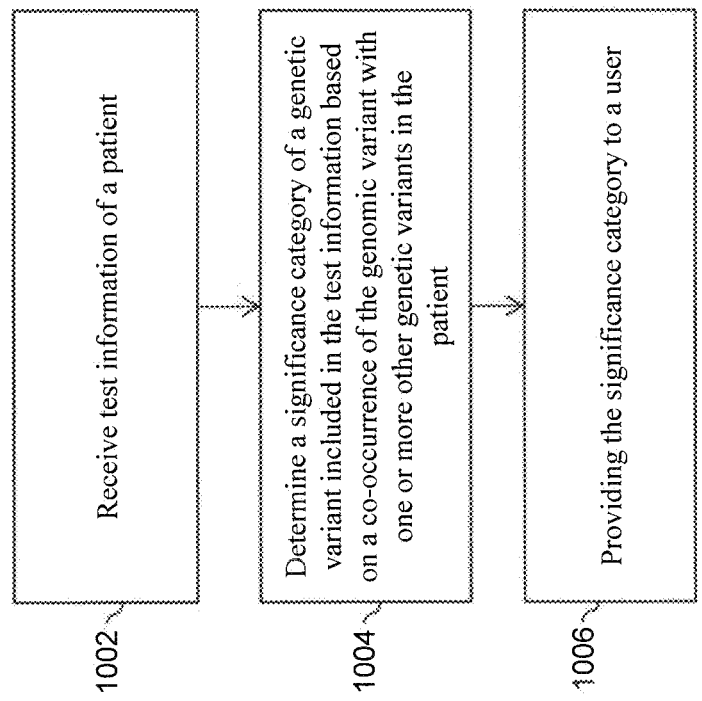
FIG. 10 is a flowchart for multi-variant classification, according to an embodiment.
Figure 11:
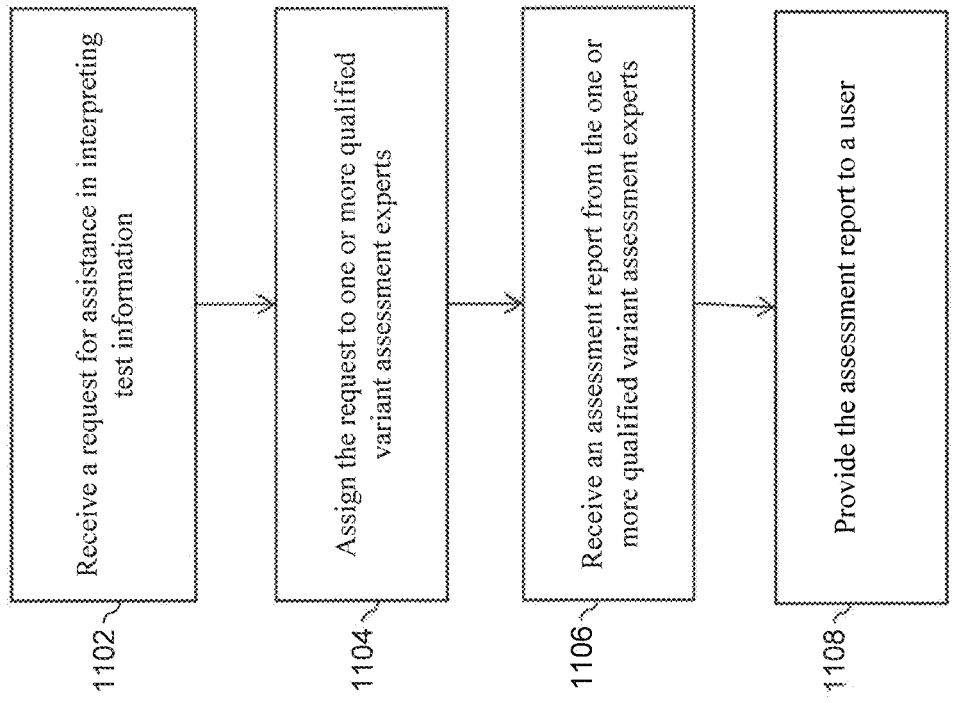
FIG. 11 is a flowchart for validating an assessment, according to an embodiment.

As described above, a single variant may be linked to a particular phenotype, such that a patient having the variant is likely to express the particular phenotype. But it is not always that simple—many patients exhibit multiple genetic mutations, and the combined effects of those mutations (or lack thereof) may need to be considered, for example, to obtain a true picture of that patient's health and/or treatment options. Modifier variants and genetic background can dramatically impact the degree to which a particular variant is correlated with manifestation of a given phenotype in a particular patient, such as disease or response to drug treatment. FIG. 10 is a flowchart of a method 1000 for multi-variant classification, according to an embodiment. Method 1000 can be performed by processing logic that includes hardware (e.g., circuitry, dedicated logic, programmable logic, microcode, etc.), software (e.g., instructions run on a processing device), or a combination thereof. In an embodiment, method 1000 is performed by computing system 102.

In block 1002, test information of a patient is received. In an embodiment, computing system 102 receives the test information. Test information can be received from one or more sources. For example and without limitation, test information can be received from a test subject, a laboratory, a care provider, insurer, etc.

In block 1004, a clinical assessment or significance category of a genomic variant included in the test information is determined based in part on a co-occurrence of the genomic variant with one or more other genomic variants it the patient. In an embodiment, computing system 102 determines the significance category. Alternatively or additionally, an existing significance category of the genomic variant included in the test information can be modified based on the co-occurrence of the genomic variant with one or more other genomic variants in the patient.

In an embodiment, determining the significance category uses information in a knowledge base about the genomic variant and one or more other genomic variants. The information can be structured according to an ontology. A knowledge base may identify links between the genomic variant and one or more other genomic variants. In an embodiment, such modifier variant information is derived from evidence curated from the biomedical literature, structured according to an ontology. In an embodiment, such modifier variant information is derived from a database of patient test information that enables correlation of genotypic information and phenotypic information to identify variants that are highly probable to modify the severity (or presence/absence) of a phenotype. For example, references that discuss interactions between variants can impact a clinical assessment of a given variant, and is subject to change based on other variants that are observed in that patient or new literature or database evidence that enters the knowledge base over time. This is fundamentally different than clinical assessment using single variants independently without regard for presence or absence of other modifier variants in the patient's test information.

For example, a particular genomic variant may be fairly benign when appearing on its own, but pathogenic in combination with other genomic variants. Alternatively, a variant may be pathogenic in one patient, but benign in another patient who has one or more other variants that mitigate the potential negative impacts of the first variant. So, patient test information identifying a particular variant on its own may be assigned to one significance category, but patient test information identifying the same variant in combination with other variants may be assigned to a different significance category than if said variants were assessed independently. In an embodiment, the clinical assessment of a first variant having one or more known modifier variants would be assigned to a clinical significance category based not only on evidence associated with said first variant, but based on comprehensive assessment of that variant in combination with modifiers that are present or absent in that patient's test information. The specific significance category assigned may be determined based on information about the multi-variant relationships obtained from the knowledge base.

In one embodiment, a given variant of interest could be assessed according to the American College of Medical Genetics guidelines for variant scoring. The scoring guidelines may be implemented as a series of computer-based rules, in which the rules may be assigned various weights or significance levels. This computer-based scoring logic may be then extended to include computer-based assessment of literature in a knowledge base for other modifier variant sites that are known to genetically interact with the variant of interest to modify the phenotype. The knowledge base of curated literature may be queried to determine whether or not cases have been documented wherein patients have the variant of interest as well as one or more sequences at other sites that are known or believed to modify the severity or nature of the phenotype typically caused by the variant of interest.

For example, if the CFTR delta-F508 mutation can be scored to assess a patient's risk for cystic fibrosis, but the patient has a sequence variant (or lack of a variant) at another position in the genome that has been documented in the literature to mitigate or eliminate the cystic fibrosis phenotype in patients with homozygous delta-F508 mutations, a rule would trigger that changes the variant classification for the delta-F508 mutation from "pathogenic" to a less severe category depending on the quality and quantity of literature or database evidence supporting the modifier variant. The modifier variant may be in the same gene as the variant of interest, or it may be in a different gene.

In an embodiment, a database of cystic fibrosis patient cohorts may be analyzed to assess whether unaffected individuals homozygous for delta-F508 possessed the modifier sequence, and whether this modifier co-segregated with disease-free status among patients with homozygous delta-F508 mutations, which would typically be assessed as disease-causing. Papers, such as "Exome sequencing of extreme phenotypes identifies DCTN4 as a modifier of chronic Pseudomonas aeruginosa infection in cystic fibrosis," may indicate that such modifier variants are likely to exist. The techniques for multi-variant classification discussed herein are able to leverage curated evidence from the biomedical literature, structured according to an ontology, to modify the classification of a variant of interest based on a ruleset.

In an embodiment, the patient can be assessed for cancer treatment options, but the modifier sequence or sequences (such as variants or lack thereof) can modify the assessed treatment options for this patient. For example, a patient with late-stage melanoma may test positive for the BRAF V600E variant, which is typically associated with more favorable outcomes upon treatment with vemurafenib. However, the assessment may be modified by one or more other variants (or lack of variants) in BRAF or in other genes that are known or believed to modify patient response to vemurafenib in the biomedical literature, clinical trials, and/or prescribing information approved by one or more regulatory agencies. The presence of modifier variants in the patient's test information can modify variant assessments and/or test results, including but not limited to modification of the test result bibliography to include papers relevant to the interaction between and among the variant of interest and other sequence variants (or lack thereof) that modify the phenotype or phenotypes typically caused by the variant of interest.

In an embodiment, determining the significance category uses a rule-based assessment. The rule-based assessment can process one or more rules to categorize the genomic variant. For example, a ruleset for assessment of variants for hereditary disease might be used to classify a variant as pathogenic, likely pathogenic, unknown significance, likely benign, or benign. Such a ruleset might include rules of varying weight. A rule might state that a variant of interest that has an allele frequency in a population unaffected by an associated phenotype is very unlikely to be causal for that phenotype. Such a rule could be strong evidence in favor of a benign or likely benign classification. Alternatively, the classification categories for a ruleset could be customized and tailored to a particular application of interest to a physician, individual or institution. For example, a ruleset might be used to assess variants for their degree of clinical significance in treating a particular form of cancer. In one non-limiting example, classification categories for a cancer sequence-based test interpretation application may include clinically relevant (same tissue), clinically relevant (different tissue), clinical trial associated, or cancer pathway associated.

In an embodiment, a rule for interpretation of cancer variants might state that if a variant is directly referenced by the prescribing information for a drug as approved by the appropriate regulatory agency (e.g., the FDA) for use to treat cancer in the tissue of interest, the variant should be categorized as clinically relevant (same tissue) with respect to this sample. For example, the FDA's website includes a description of drugs based on mutations observed in the EGFR gene. This can be an extremely strong line of evidence. The system evaluates those rules and their strength of evidence and provides a computed classification back to the user or the reviewer.

For example, a classification computed by the system based on the information available in the knowledge base may label a variant as potentially benign or likely benign. Such an assessment is based on evidence in the knowledge base showing that a first variant co-occurs in the same patient with a second variant that mitigates the phenotype typically associated with the first variant. That is, another DNA mutation in this patient is causing this patient to likely not suffer from the typical disease or harmful effects of the first variant. Even though the first variant is pathogenic in 99% of people, the first variant is known not to be pathogenic in such multi-variant patients based on existing evidence.

In an embodiment, the one or more other genomic variants are known to confer additional sensitivity or resistance to phenotypic effects of the genomic variant. For example, the knowledge base can have references that discuss the relationships between genetic variations that demonstrate the additional sensitivity or resistance to phenotypic effects. These relationships can be stored as structured information in a knowledge base, e.g. structured according to an ontology. In an embodiment, the variant is at least one of a somatic variant in oncology or a heredity variant that predisposes the patient to a genetic disorder.

In block 1006, the significance category is provided to a user. In an embodiment, computing system 102 provides the significance category to the user. The user can agree or disagree with the computed significance category. In an embodiment, if a reviewer disagrees with the computed significance category, the reviewer can modify it. Continuing the example above that returns a category of "likely benign," the reviewer may suggest another classification, such as "likely pathogenic," and still include it in his report, but with an added note as to why the reviewer agrees or disagrees with categorization.

Providing an Expert Assessment of Test Information

A user may use portal 105 to request that an expert assess a patient's test information. FIG. 1100 is a flowchart of a method 1100 for providing an expert assessment to a user, according to an embodiment. Method 1100 can be performed by processing logic that includes hardware (e.g., circuitry, dedicated logic, programmable logic, microcode, etc.), software (e.g., instructions run on a processing device), or a combination thereof. In an embodiment, method 1100 is performed by computing system 102.

In block 1102, a request for assistance in interpreting the test information is received from a user. The request may include a specific patient's test information. Alternatively or additionally, the request may reference test information that is already stored in the knowledgebase. In an embodiment, computing system 102 receives the request.

In block 1104, the request is assigned to one or more qualified variant assessment experts. In an embodiment, computing system 102 assigns the request, which can be accessed by an expert over network 106. A qualified variant assessment expert may be an individual that has achieved a particular expertise in preparing, performing, or reviewing variant assessments. An expert can be certified as such by a certifying body, or by satisfying a set of criteria. One of skill in the art will recognize that the set of criteria to be satisfied may change depending on, for example, the variant or variants being assessed and/or depending on the phenotype or phenotypes affecting the patient. Computing system 102 may notify the expert when an assessment has been assigned to the expert.

In block 1106, a completed assessment report is received from the one or more qualified variant assessment experts. In an embodiment, computing system 102 receives the assessment report from the expert over network 106. An assessment report can include one or more clinical significance assessments of one or more genomic variants contained in the test information. The expert may have prepared all or a part of the report.

In block 1108, the assessment report is returned to the requesting user.

In an embodiment, as mentioned above, an expert may be enrolled and certified by an organization. The organization can build a network of experts and take a finders' fee for linking users with an appropriate certified expert to help them with the needed interpretation. For example, a user can load the test information into the system via portal 105, and the user can request, for example via a prompt, expert assistance in interpreting the test information. The test can then be assigned to one or more qualified experts for assessment. In an embodiment, the expert conducts the analysis on his own. In another embodiment, the expert conducts the analysis side-by-side with the user, by sharing the test information in the context of the system and/or communicating with the user. The expert can then provide a report to the user including the assessment of the variants that were contained in test information that was assessed by the expert.

Correlating Genotype to Phenotype

Figure 12:
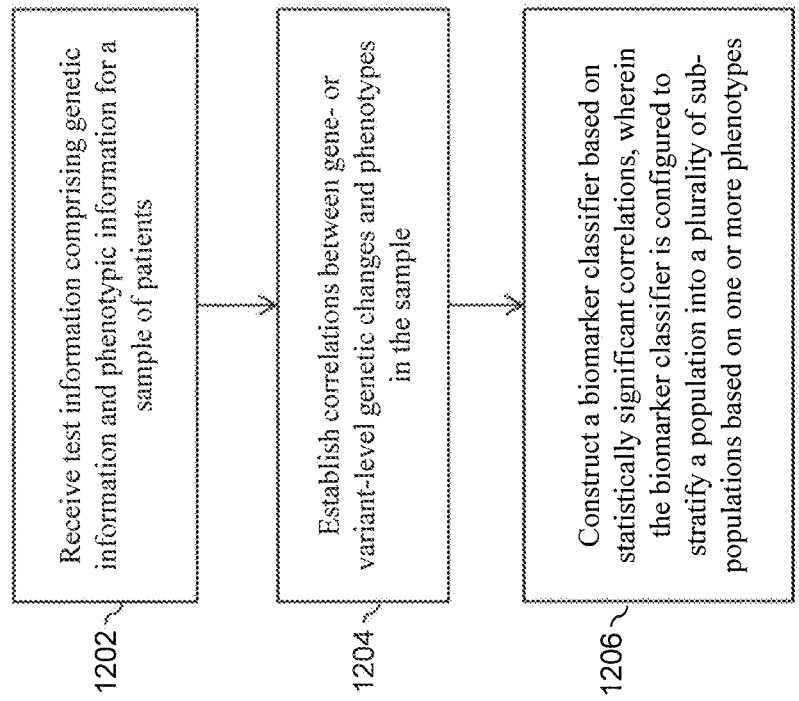
FIG. 12 is a flowchart for correlating a genotype to a phenotype, according to an embodiment.

As more information is provided to the knowledge base, large scale patterns in the data can be determined, linking particular genetic signatures to phenotypes. FIG. 12 is a flowchart of a method 1200 for correlating a genotype to a phenotype, according to an example embodiment. Method 1200 can be performed by processing logic that includes hardware (e.g., circuitry, dedicated logic, programmable logic, microcode, etc.), software (e.g., instructions run on a processing device), or a combination thereof. In an embodiment, method 1200 is performed by computing system 102.

Genotype or phenotype correlation can include linking genetic changes to phenotype. For example, this includes determining that a mutation is associated with a particular disease or is associated with a good response to a particular drug treatment. Test information can be collected over time and from multiple organizations for the analysis.

In block 1202, test information including genetic information and phenotypic information for a sample of patients is received. In an embodiment, computing system 102 receives the test information from a plurality of clients 104 over network 106. The phenotypic information can be structured according to an ontology, so that cross-correlations that would be notoriously difficult in unstructured knowledge collections can be conducted. Each patient in the sample of patients may need to have provided consent to use their test information in this type of analysis. Patient consent can also be included in the received test information.

In block 1204, correlations between gene- or variant-level genetic changes and phenotypes in the sample are established. In an embodiment, computing system 102 establishes correlations between pathway-, gene- or variant-level genetic changes by identifying patterns in the test data.

In block 1206, a biomarker classifier is constructed based on statistically significant correlations. In an embodiment, computing system 102 constructs the biomarker classifier. In an embodiment, one or more users supervises and informs construction of the biomarker classifier. A biomarker classifier can be configured to stratify a population into a plurality of subpopulations. For example, the biomarker classifier can be applied to each patient's test information to determine a sub-population to which the patient belongs. The biomarker classifier may be created using one or more of the following techniques. The biomarker classifier can be developed using a statistical method, such as the Sequence Kernel Association Test (SKAT). Alternatively or additionally, the biomarker classifier can be created using a clustering method such as k-means or hierarchical clustering. These techniques may be applied at the variant, gene, and/or pathway level to identify statistically significant associations between genetic changes and observed phenotype. These techniques can be used to source phenotypic and genotypic information from multiple users across multiple datasets and populations. For samples that have the appropriate consent, the system can identify genotype-to-phenotype associations that are statistically significant in a meta-analysis performed across multiple studies performed by multiple users.

In an embodiment, the sub-populations include a sub-population that is more susceptible to a rare adverse event following therapeutic treatment and a sub-population that is less susceptible to the rare adverse event following therapeutic treatment. In another embodiment, the sub-populations include a sub-population of likely responders to therapy and a sub-population of unlikely responders to therapy. In another embodiment, the sub-populations include a sub-population of individuals more likely to be affected by a disease and a sub-population of individuals less likely to be affected by the disease. In another embodiment, the sub-populations are ethnic groups. One of skill in the art will recognize that a population may be separated into additional or other populations than those described above.

In an embodiment, a report with the results of the classification is provided to the user. The report can also include the biomarker classifier used, a confidence level of the classifier, and the like.

Figure 13:
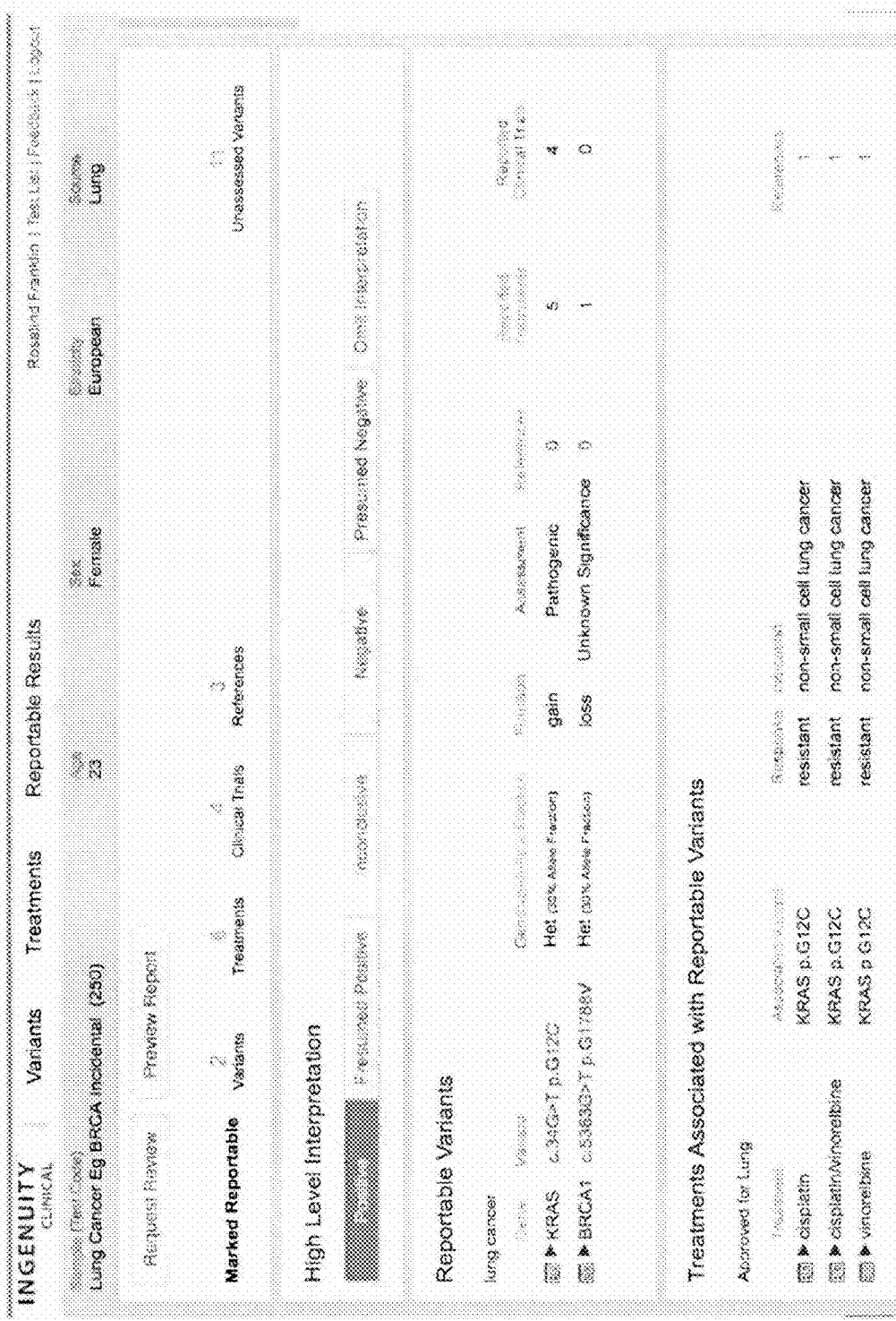
FIG. 13 depicts an example report that includes the classification of a user, according to an embodiment.

FIG. 13 depicts an example report 1300 that includes the classification of a user. Report 1300 includes information about the test performed, a high-level interpretation, reportable variants, and treatments associated with reportable variants. Although FIG. 13 provides an example report 1300, embodiments of the invention support other types or arrangements of reports, in which any information related to the user classification can be presented to a patient or other user, including but not limited to any of the information discussed herein.

Ethnically-Matched Controls

Figure 14:
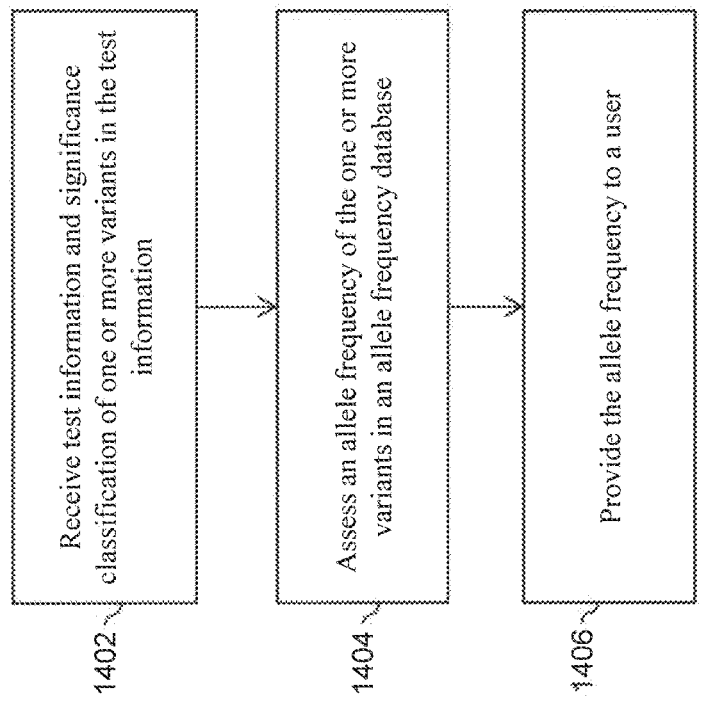
FIG. 14 is a flowchart for assessing allele frequency, according to an embodiment.

The diversity of many clinical test or research participants is lower than the general population. Additionally, genomic variants may be commonly observed in individuals from a first ethnic background, but not in individuals from a second ethnic background. So, if a user truly wishes to know whether a variant is causal for a given phenotype in a given patient (as opposed to a benign polymorphism), that user must evaluate the variant with respect to a variety of individuals unaffected by the phenotype of interest, including a large number of individuals who are ideally of the same ethnic background as the patient. This allows the user to be relatively confident that a rare variant observed in a patient affected by a rare disease is actually rare in that patient's ethnic population (as opposed to rare in the general population, but relatively common in the patient's ethnic population). FIG. 14 is a flowchart of a method 1400 for assessing allele frequency, according to an example embodiment. Method 1400 can be performed by processing logic that includes hardware (e.g., circuitry, dedicated logic, programmable logic, microcode, etc.), software (e.g., instructions run on a processing device), or a combination thereof. In an embodiment, method 1400 is performed by computing system 102.

In block 1402, test information and a significance classification of one or more variants in the test information is received. Test information and significance classification can be received from one or more sources, such as a test subject, a laboratory, a care provider, insurer, etc.

In block 1404, an allele frequency of the one or more variants in an allele frequency database is assessed. In an embodiment, the allele frequency database is located in storage 110.

In an embodiment, the allele database has at least a minimum number of data points. For example, the database may be required to include sequence information derived from at least 10,000 individuals, including at least 500 individuals from at least 40 different ethnic groups.

In an embodiment, the allele frequency database includes frequencies of the one or more variants for a plurality of sub-populations. The sub-populations can include, for example and without limitation, the following ethnic groups: Caucasian, Hispanic, Indian, Filipino, Puerto Rican, African, Pacific Islander, Native American, Turk, Gulf/Middle Eastern, Parsi, Chinese, Malaysian, Ashkenazi Jew, New Zealand, Korean, Japanese, and Aboriginal Australian.

In block 1406, the allele frequency is provided to a user. In an embodiment, computing system 102 provides the allele frequency to the user.

In an embodiment, the significance classification of the one or more variants is modified from the norm based on the allele frequency. The classification can be modified to be more or less severe. The assessed frequency of a variant can be compared against the general frequency in the population. The real frequencies of present test information and of the real frequency database can be provided to the user. Putting test results into ethnic context result in a correction of the causal correlation for a phenotype attributed to a genomic variant. For example, the classification of a variant can be modified from a more severe classification to benign for variants that are present at an allele frequency in an un-diseased population that is too high to reasonably explain a patient's phenotype.

For example, consider a particular BBS1 variant, which is a variant that causes Bardet-Biedl syndrome (BBS). BBS1 is a gene that when mutated can cause a disease called Bardet-Biedl syndrome. This variant occurs in 0.2% of individuals based on the frequency, and the prevalence of this disease is about 1 in 70,000. From this information, the most one would expect this variant to be seen in the general population is at 0.3%. This is consistent with the observations of the variant at 0.2%. But if the database does not include statistically significant information from a particular ethnic group, then it will be unclear whether the variant has the same level of occurrence in that ethnic group as the general population, or whether there is something genetically special about that ethnic group. For example, consider the scenario in which the system returns a variant observation of 20% in a population of Puerto Ricans, where the maximum value in the general population would be expected to be 0.3%. It raises the question of whether the variant is more prevalent in Puerto Ricans or whether there are simply not enough Puerto Ricans in the database to conduct a statistically significant analysis. Using an allele frequency database having specific requirements for data points from multiple ethnic groups including but not limited to large groups of sequenced individuals representing ethnic groups of patients being clinically assessed remedies these issues.

Scoring a Variant

Figure 15:
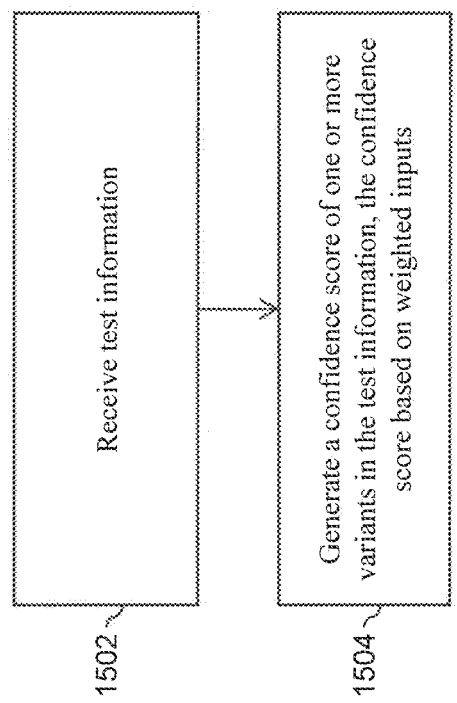
FIG. 15 is a flowchart for scoring a variant, according to an embodiment.

Sequence-based tests can potentially generate millions of observed variants in a single patient. It can be complex to determine which variants are most likely to be relevant or important in the assessment or treatment of a patient from those that are not. Variant assessments may be scored to provide a user with a confidence level reflecting the depth of information relevant to the particular variant of interest. FIG. 15 is a flowchart of a method 1500 for scoring a variant, according to an embodiment. Method 1500 can be performed by processing logic that includes hardware (e.g., circuitry, dedicated logic, programmable logic, microcode, etc.), software (e.g., instructions run on a processing device), or a combination thereof. In an embodiment, method 1500 is performed by computing system 102.

In block 1502, test information of a patient is received. In an embodiment, computing system 102 receives the test information from one or more sources. For example, test information can be received from, for example and without limitation, a test subject, a laboratory, a care provider, insurer, etc.

In block 1504, a confidence score of one or more variants in the test information is generated based on weighted inputs. In an embodiment, computing system 102 generates the confidence score. The inputs that are weighted can include any combination of, for example and without limitation: a frequency of the one or more variants in a population of individuals unaffected by the patient's disease phenotype including ethnically-matched individuals, an association of the one or more variants with a phenotype in a knowledge base, sequencing coverage at a site of the one or more variants, and call confidence of the one or more variants reported by variant calling software. The weight given to each input can be set using predetermined values, adjusted values based on the strength of the inputs, or any combination thereof. For example, the frequency of the one or more variants in a population of individuals unaffected by the patient's disease phenotype including ethnically matched individuals may be determinative if the frequency is associated with a high confidence value for disease-association. As discussed above, if a variant is extremely common, particularly within a patient's ethnic sub-population, then the likelihood of that variant being causal for a rare disease in said patient is low.

An association of the one or more variants with a phenotype in a knowledge base can include a measure of how frequently the variant is associated with a phenotype in the literature in a knowledge base. Sequencing coverage at a site of the one or more variants may refer to a measure of how many times the variant has been sampled, where the variant is only a portion of other nucleotides in the genome. For example, in 1× coverage there is only one data point that this variant exists, which could indicate extremely poor quality. On the other hand, as coverage increases (e.g. 100× coverage, 1000× coverage, or 3000× coverage) the results can be increasingly relied upon.

In an embodiment, a call confidence of the one or more variants can be reported by alignment and/or variant calling software, which generally generate a quality score of the trustworthiness of the analysis performed by the software. For example, the alignment and variant calling software can be the CLC Bio Genomics Workbench. As another example, the alignment and variant calling software could be BWA/GATK (Burrows-Wheeler Aligner/Genome Analysis Toolkit).

In an embodiment, the inputs can be weighted according to a decision tree. In some instances, the decision tree can prevent an input from contributing to the confidence score.

Providing a Variant Classification Alert

Figure 16:
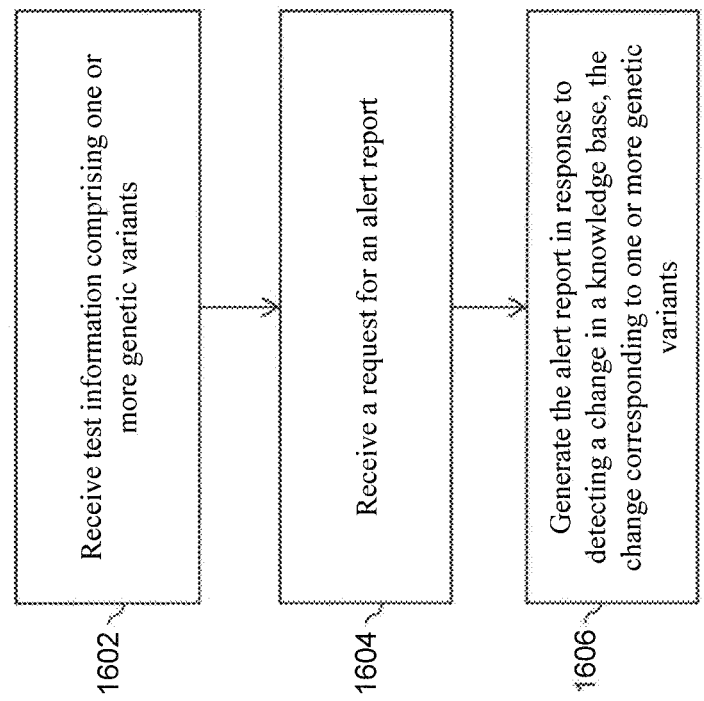
FIG. 16 is a flowchart for providing a variant classification alert, according to an embodiment.

When information about a particular genomic variant is added, updated, or changed in the knowledge base, for example with regard to clinical assessment significance category, clinical trial information, treatment information, and/or bibliography, a user may wish to receive an alert. FIG. 16 is a flowchart of a method 1600 for providing a variant classification alert, according to an embodiment. Method 1600 can be performed by processing logic that includes hardware (e.g., circuitry, dedicated logic, programmable logic, microcode, etc.), software (e.g., instructions run on a processing device), or a combination thereof. In an embodiment, method 1600 is performed by computing system 102.

In block 1602, test information including one or more genomic variants is received. In an embodiment, computing system 102 receives the test information from one or more sources. For example, test information can be received from, for example and without limitation, a test subject, a laboratory, a care provider, insurer, etc.

In block 1604, a request for an alert report is received from a user. The alert report may identify a particular genomic variant that a user is interested in. The request for an alert report may be stored by computing system 102 along with other alert report requests from the same or different users.

In block 1606, the alert report is generated in response to detecting a change in a knowledge base, the change corresponding to one or more genomic variants. In an embodiment, computing system 102 monitors the information in the knowledge base of storage 110, and generates the alert report when an add, change, or update event is detected.

In an embodiment, the report can be generated at any interval. For example, the alert report can be generated at a frequency of at least once every two years or at a frequency of once per day, or at a frequency of once per week, or at a frequency of once per month, or at a frequency of once per year. In an embodiment, the report can be generated when a significant change in the knowledge associated with one or more variants of interest occurs. In an embodiment, variants of interest to a user may be inferred based on variants associated with phenotypes contained in that user's test information.

In an embodiment, the alert report summarizes changes to a classification of the one or more variants since a previous variant classification was generated or otherwise provided to a third party as part of a clinical report.

In an embodiment, the alert report is provided to a user, for example, by computing system 102. Providing the alert report may refer to any action that facilitates delivery of the alert report to the user. For example, providing the alert report may be performed by notifying the user that the alert report has been generated, sending the alert report electronically to the user, providing the user with the alert report at computing system 102, alerting the user to access a patient portal, or any combination thereof.

Figure 17:
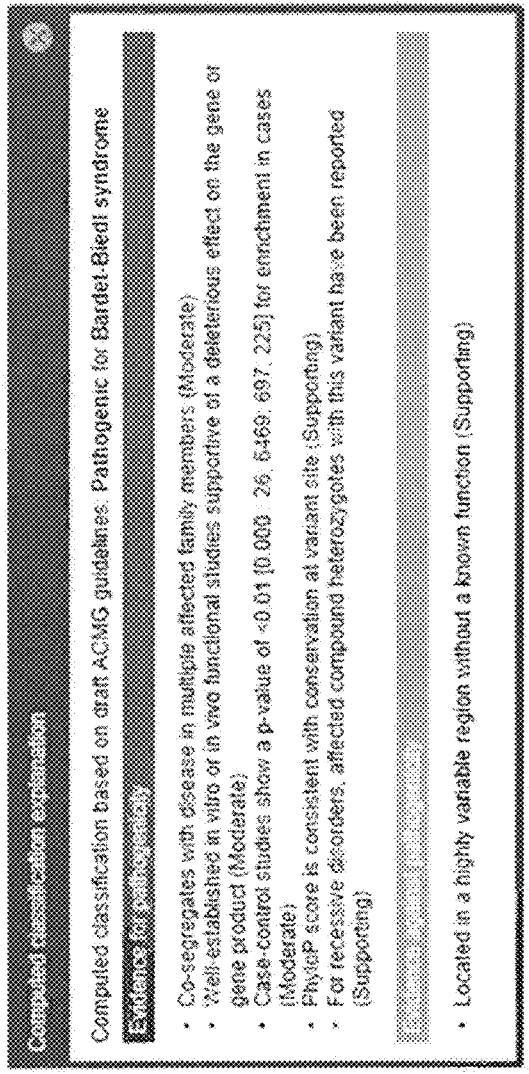
FIG. 17 depicts an example alert report, according to an embodiment.

FIG. 17 depicts an example alert report 1700. Alert report 1700 includes a variant identifier, a prior classification of the variant, a new or updated classification of the variant, a date of the update, and a summary of evidence that lead to the change in classification. Although FIG. 17 provides an example alert report 1700, embodiments of the invention support other types or arrangements of alert reports, in which any information related to the variant change can be presented to a patient or other user, including but not limited to any of the information discussed herein.

Patient Portal

Figure 18:
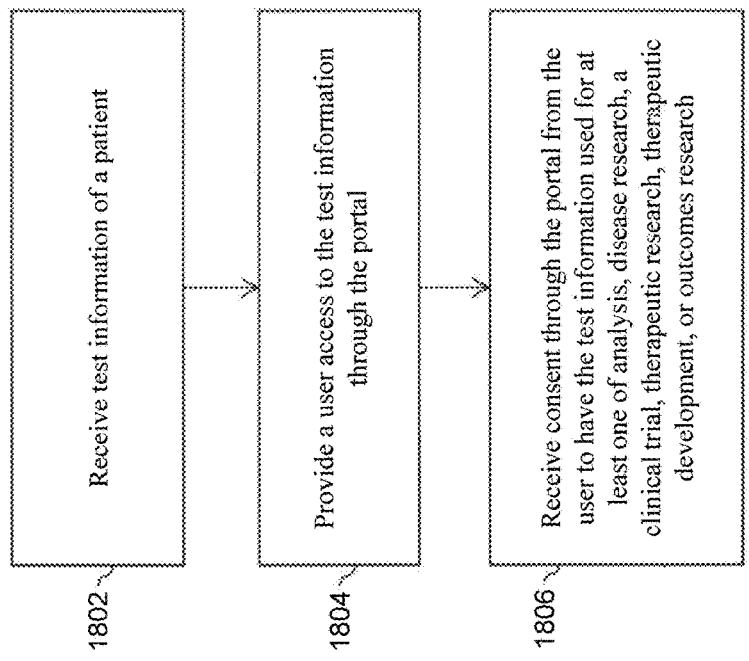
FIG. 18 is a flowchart for providing a patient portal, according to an embodiment.

Most of the previous discussion has involved examples where the user is a physician, researcher, laboratory technician, pharmaceutical company, and the like. However, patients themselves may be interested in accessing the information stored in the knowledge base. FIG. 18 is a flowchart of a method 1800 for providing a patient portal, according to an embodiment. Method 1800 can be performed by processing logic that includes hardware (e.g., circuitry, dedicated logic, programmable logic, microcode, etc.), software (e.g., instructions run on a processing device), or a combination thereof. In an embodiment, method 1800 is performed by computing system 102.

In block 1802, test information of a patient is received, for example by computing system 102. The test information can be stored in the knowledge base. The test information can be received from any source, such as the patient or an authorized provider.

In block 1804, access to the test information through the portal is provided to a user. In an embodiment, computing system 102 notifies the patient or an authorized provider that access to the test information has been granted. In an embodiment, the user may be any one that accesses the portal, such as the patient, a provider, a patient's family member, friend, agent, or representative, physician, an insurer, or any combination thereof.

In block 1806, consent is received through the portal from the user to use the test information. The consent may be for using the test information for at least one of analysis, disease research, clinical trial matching, therapeutic research, therapeutic development, outcomes research, public release, release to a requesting party, or any purpose. In an embodiment, computing system 102 receives the consent from the user.

In an embodiment, the user is authenticated prior to being provided access to the portal. Authentication can include, for example, logging into the system.

In an embodiment, the test information associated with the user includes genetic information, supporting annotations that have become available after the test information was generated, and/or the like. This information can be provided to the user as it is made available on the portal. For example, this embodiment can be provided as an alert report on the portal.

Access to the portal can be provided based on fulfilling conditions. In one embodiment, access to the portal is governed by payment of a subscription fee. In another embodiment, access to the portal is predicated on consent to usage terms for the test information associated with the user. In another embodiment, access to the portal is predicated on consent to receive targeted advertisements or offers based on test information. In another embodiment, access to the portal is predicated or consent to release anonymous summary statistics computed based upon patient's test information, such as allele frequency information within the general population and/or a particular ethnic subpopulation.

A user's interactions with the portal can be used to determine information about the user. In an embodiment, the user's access to the portal is monitored. It can be determined that the user would qualify for enrollment in a clinical trial based on monitoring the access. For example, the user's access to the portal can indicate certain things about, for example and without limitation, the user's health status, the user's location, the user's availability, and the user's interest in such information. This type of status information may not be as readily available from sources other than the portal, and can be, among other factors, a qualification for enrollment in a clinical trial. A user can also upload treatment history and genotypic information into the portal that could be used to match the user with clinical trials that could benefit the user.

FIG. 19 depicts an example patient portal 1900. In an embodiment, patient portal 1900 is provided by computing system 102. Patient portal 1900 displays test information related to a patient. For example, patient portal 1900 shows whether or not the patient has relevant EGFR mutations to FDA-approved targeted therapies. Patient portal 1900 also displays several drug therapies, including treatments, a characterization of the treatments' success, and indications associated with the treatment. Patient portal 1900 also displays clinical trials associated with the genomic variant.

Although FIG. 19 provides an example of patient portal 1900, embodiments of the invention support other types or arrangements of patient portals, in which any information related to the patient can be presented to a patient or other user, including but not limited to any of the information discussed herein.

Variant Classification Rules Improvement

Figure 20:
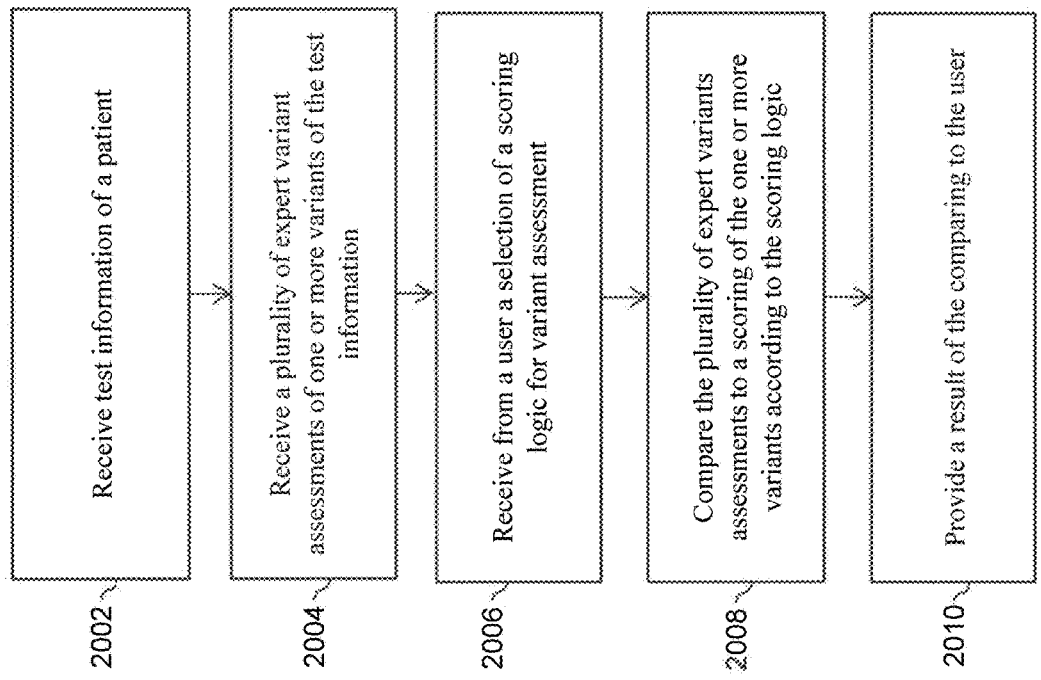
FIG. 20 is a flowchart for improving a variant classification rule, according to an embodiment.

FIG. 20 is a flowchart of a method 2000 for improving a variant classification rule, according to an example embodiment. Method 2000 can be performed by processing logic that includes hardware (e.g., circuitry, dedicated logic, programmable logic, microcode, etc.), software (e.g., instructions run on a processing device), or a combination thereof. In an embodiment, method 2000 is performed by computing system 102.

In block 2002, test information of a patient is received. In an embodiment, computing system 102 receives the test information of a patient. Test information can be received from one or more sources. For example, test information can be received from, for example and without limitation, a test subject, a laboratory, a care provider, insurer, etc.

In block 2004, a plurality of expert variant assessments of one or more variants of the test information is received. The expert variant assessments can be received from one or more sources, including, for example and without limitation, a laboratory, a care provider, an insurer, a research institution, etc. The expert variant assessments can use any scoring logic for evaluation of the variant, e.g. the American College of Medical Genetics (ACMG) rules for variant assessment, any of the scoring logics discussed herein, any other scoring logic, or any combination thereof. In an embodiment, the expert variant assessments are manual assessments of the variant.

In block 2006, a selection of a scoring logic for variant assessment is received. The scoring logic for variant assessment can be any type of scoring logic, e.g. the ACMG rules for variant assessment, any of the scoring logics discussed herein, any other scoring logic, or any combination thereof. In an embodiment, the scoring logic is selected in advance. In an embodiment, the scoring logic is selected based on a particular test offering.

In block 2008, the plurality of expert variant assessments is compared to a scoring of the one or more variants according to the scoring logic.

In block 2010, a result of the comparing is provided to the user. The results of the comparing can include a degree of correlation between the plurality of expert variant assessments and the scoring according to the scoring logic. This degree of correlation can demonstrate how similar or dissimilar the scoring logic is to the expert assessments. The result can also be used in a feedback loop to improve the scoring logic of computing system 102 using, for example, standard machine learning processes.

Pooling Allele Counts or Frequencies

As variant analysis techniques have become more sophisticated, they rely increasingly on a larger number of and more diverse dataset of variant samples to tease out meaningful relationships between the variants and phenotypes. However, traditional sources of variant data suffer from sample sets that are too small, from ethnic bias, or both. For example, projects such as the Exome Variant Server (EVS) Project and the 1,000 Genomes Project presently have genome information numbering in the thousands, but no more than 10,000. The datasets are ethnically biased toward Caucasians, with datasets for ethnic subpopulations (e.g. Puerto Rican) that are too small to enable identification of common polymorphisms in these subpopulations. Larger and more diverse databases of allele statistics, such as pooled frequencies and observation counts, make it easier to distinguish potential rare disease-causing variants from benign variants. Such databases therefore can benefit clinical interpretation of sequence-based tests, as well as translational research with goals of, for example, identifying novel disease causing variants and genetic biomarkers for diagnosis and patient stratification. The problems of traditional databases are caused in part by restrictions on and reluctance to share human genetic information. Due to the limitations of traditional sources of public variant data, any analysis using this data has a high risk of misinterpreting variants in patients who are part of an ethnic population that is under represented in public sequence databases.

The techniques described herein overcome these shortfalls by combining allele statistics from across a wider range of consented samples to provide enhanced allele counts or frequency coverage. Collecting data during variant analysis workflows makes it more convenient for researchers and clinical labs to share information in a useful way, so larger numbers of samples become content in and of themselves for interpretation of genotypes. Furthermore, by providing a mechanism for users to share anonymous, pooled allele statistics such as counts or frequencies rather than more complete genomic information, embodiments can make users more comfortable sharing the genomic information. Users are generally less comfortable sharing complete genomic information and more comfortable sharing genomic information that is pooled and anonymized. Embodiments also provide an incentive for users to share genomic information, designed to overcome tendencies to hoard data without giving back to the community. For example, the system may only permit a given user's genomic dataset to be annotated with pooled allele statistics if that user has also consented to "contribute" and allow their own genomic dataset to contribute to the pool, thereby enhancing discovery power for that user as well as all other users whose datasets are "opted-in" or consented to participate in the community. Leveraging the combination of datasets from a community of users provides more complete and representative information about variant distributions, such as allele counts or frequencies. This enables enhanced capabilities for analyzing genetic information, such as more efficient clinical sequence-based test interpretation and faster, more accurate identification of disease-causing variants. Further, enabling sharing at a pooled level mitigates the risk that individual patients will be personally identified based on their contribution to the pool. Because this level of sharing is less risky, users are both more comfortable and more likely to share their genetic information. In one embodiment, pooled variant statistics are broken into subpools, for example by sample phenotype or ethnicity/ancestry. In this embodiment, a user analyzing a sequence-based test for a patient of Puerto Rican descent may be provided with allele statistics that show that, although a particular variant of interest is extremely rare in the global population, it is in fact very common in the Puerto Rican population and therefore unlikely to be disease-causing in this patient.

As used herein, the term "anonymized" refers to information that, by its nature, is not personally identifiable, and therefore anonymous. One of ordinary skill in the art will recognize that a pool of allele statistics from a plurality of individuals without personally identifiable information is, by its nature, anonymized or anonymous in nature, and that although additional steps may be taken to ensure individual privacy, the act of calculating allele statistics from a pool of individuals in and of itself is able to yield anonymized allele statistics.

Figure 21:
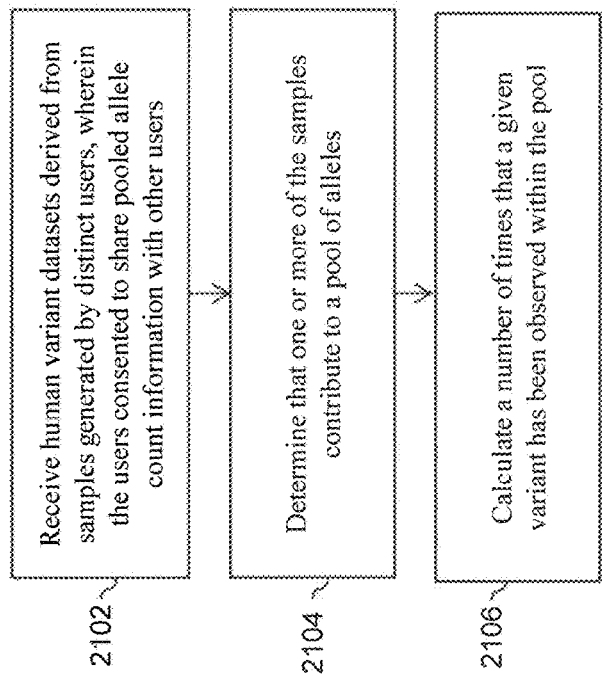
FIG. 21 is a flowchart for improving a variant classification rule, according to an embodiment.

FIG. 21 is a flowchart of a method 2100 for building a community database of allele counts, according to an example embodiment. Method 2100 can be performed by processing logic that includes hardware (e.g., circuitry, dedicated logic, programmable logic, microcode, etc.), software (e.g., instructions run on a processing device), or a combination thereof. In an embodiment, method 2100 is performed by computing system 102.

At block 2102, human variant datasets, derived from samples generated by distinct users, are received. In an embodiment, computing system 102 receives the human variant datasets from a plurality of users. The samples may be derived from a relatively large number of biological samples, such as 10,000 or more. Further, the samples may come from a variety of distinct users, such as 10 or more. A large number of samples and variety of sources lead to many of the benefits discussed above. The distinct users can include laboratories or projects that have received consent from participants to share their variant analyses or pooled statistics therefrom.

In an embodiment, the variant datasets are gathered and consented to during an interpretation workflow for variant datasets. For example, when a laboratory performs a test on a sample, the laboratory may transmit the results during the process to computing system 102, at which a tool may be used to collect, process, or interpret the results. In another embodiment, the consent may be received from the user up-front, or at the time of viewing an analysis when they are most interested to view the pooled allele statistics.

The users that provided the data to the pool have consented, either actively or passively, to share pooled allele count information with other users. Actively consenting can include, for example, a user expressly consenting by way of a dialog box presented on an interface, accepting a license agreement that includes the consent, etc. Passively consent can include, for example, use of a tool or workflow, particularly when the user is aware that use of the tool will be treated as consent to share pooled allele count information with other users. Further, consent may be acquired at one or more stages in a variant analysis workflow. For example, an option to consent can be presented to new users as they sign up to use an online tool, to existing users when they log into an online tool, as a condition to using or comparing pooled allele data, or any combination thereof.

Users may be offered one or more incentives for consenting or providing their information for sharing in the pooled data. For example, as mentioned above, consent can be used as a condition to using or comparing pooled data. Another incentive can be access to the counts or frequencies of one or more pools. Yet another incentive can be access to community-pooled allele frequencies or counts for use in interpreting variant data. Users can be granted greater access to pool information in return for submitting a greater quality or quantity of samples. These non-limiting example incentives have been presented for illustrative purposes, but it is understood that any other type of incentives can be used.

In an embodiment, the received human variant datasets are stored in a knowledge base of patient test information structured according to an ontology, such as is described above.

At block 2104, it is determined that one or more of the samples or variants therefrom contribute to a pool of alleles. In an embodiment, computing system 102 determines that the one or more samples contribute to a pool of alleles by searching the knowledge base. The determination can be made based on whether the patient information corresponding to a given sample meets one or more requirements of, or inclusion criteria for, a particular pool. A pool can be defined, for example, based on ethnicity, a phenotype, etc. If a sample's patient information is determined to meet the pool requirements or inclusion criteria, the sample can be added to the pool of alleles.

One or more samples or variants or user datasets can also be determined not to contribute to the pool of alleles, and can thus be excluded from the pool, based on exclusion criteria.

Exclusion or inclusion criteria for a sample can include, for example, breadth of genome coverage of the sample, depth of coverage of the sample, quality of the sample, quality of a sequence in which the sample is found, variant call quality, a phenotype associated with the sample, sample redundancy, variant counts, a trust metric for the source of the data, community feedback, containing a well-established disease-causing variant, manual or automated QC, or any combination thereof. Variants in a sample dataset might be excluded or included based upon variant call quality, read depth, or known association with a common technical error or failure mode, manual or automated QC, or any combination thereof. This quality control is beneficial when using data collected from multiple sources, because it helps to prevent duplicate samples from being multiply-counted, excludes incorrectly-called variants, and prevents samples with insufficient quality from being relied upon by the community. The criteria used for inclusion and/or exclusion may be used to define the pool and criteria may be adjusted over time to modify the pool.

In an embodiment, the ethnicity or disease state of one or more of the samples may be annotated. The samples may be annotated by using at least one of a principal component analysis (PCA), a user-provided annotation, biomarker-based analysis, or any combination thereof. For example, a user may provide an annotation of the ethnicity of a sample, and PCA can be used to verify the annotation, or vice versa. In an embodiment, the probable ethnicity of a sample may be used as an inclusion criterion to build an allele frequency database for a particular ethnic sub-population. In another embodiment, the annotated or inferred disease state of samples may be used to build an allele frequency database having samples unaffected by genetic disease(s) or other phenotype(s) of interest. These features may be combined to enable construction of a community allele frequency database that is particularly well-suited to filtering out common variants unlikely to be causal for a rare genetic disease in a patient of a particular ethnic background, because those variants are commonly observed in healthy members of the same ethnic population as the patient of interest. In an embodiment, such variants may be classified as "benign" or "likely benign" in the patient of interest based on this evidence from a pooled, anonymized knowledge base of allele statistics such as frequency, imputed frequency, or count.

At block 2106, allele statistics, such as a number of times that a given variant has been observed within the pool, are calculated. In an embodiment, computing system 102 calculates the number of times the given variant is observed within the pool. The pool can be defined by at least one of an ethnicity or a phenotype of the one or more samples, the inclusion or exclusion criteria discussed above, or any combination thereof. Further, an allele frequency may be generated based on the number of times that the variant has been observed in the pool. An allele frequency can be a ratio of a number of observed incidences of the given variant to a total number of samples in the pool believed to have potential to measure the given variant. The total number of samples in this ratio may be imputed based on variant coverage. For example, imputing may include determining whether sequencing information for that part of the genome of interest was sampled by detecting other variants commonly occurring in the region in the sample. Other allele statistics may also be calculated in block 2106.

The resulting allele statistics, can be used in one or more ways. The statistics can be provided to a user that contributed a sample. The statistics can be used in variant filtering or by a variant classification logic, such as those discussed herein. Access to the statistical information can be provided to a user via a web-based resource, such as the tool described herein.

Some individuals may not consent to having their information, or at least a portion of their information, added to the pool. However, partial data can reduce the integrity of the pool, as correlations with other information about the user could not be investigated. In an embodiment, a user may be required to provide an individual's entire dataset related to one or more variants, or not submit the dataset at all. That is, in such an embodiment, partial datasets are not allowed to be submitted. This allows the user to keep certain individuals or their information from being provided to the pool, while maintaining the integrity of datasets that contribute to the pool.

Example Computing System

Figure 22:
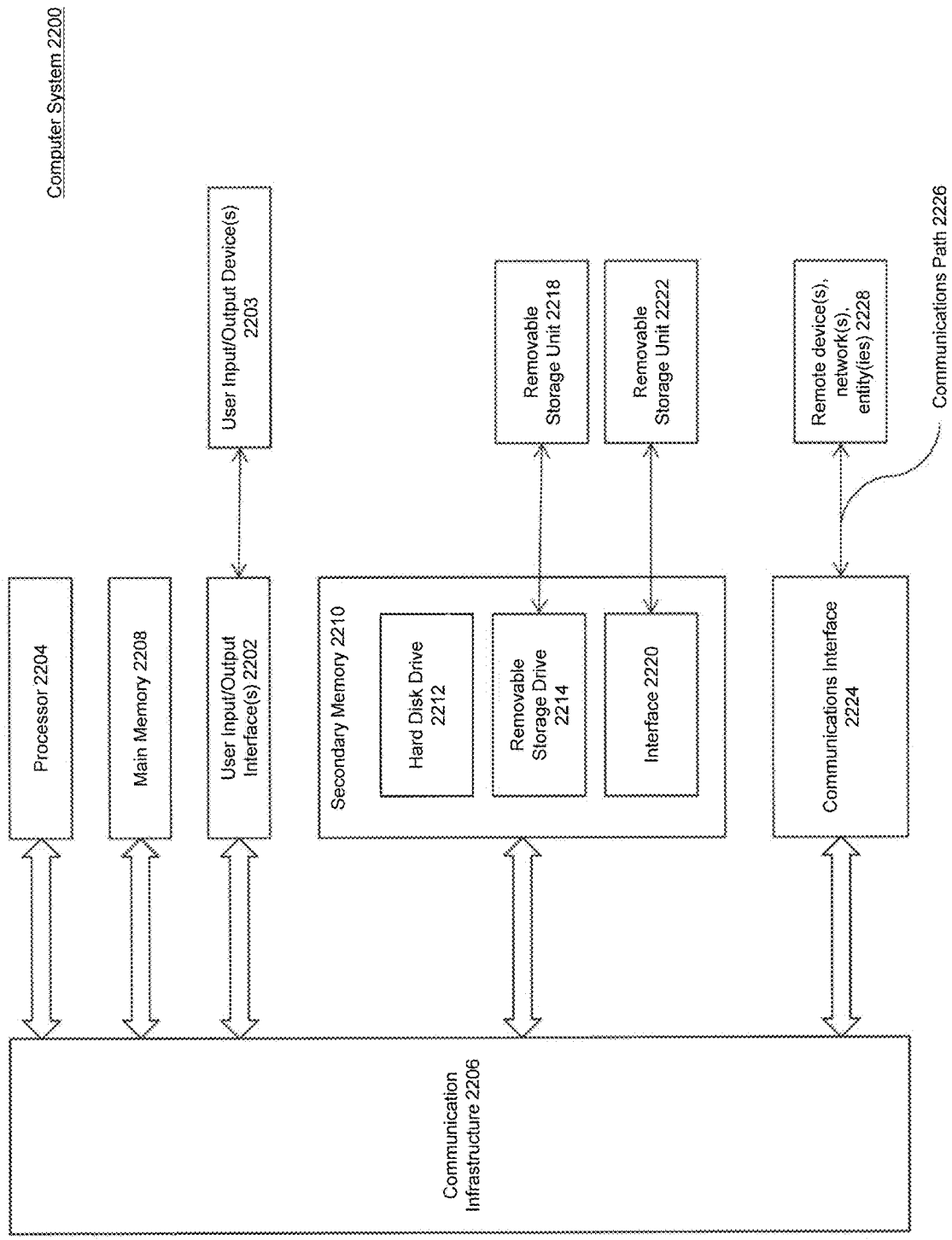
FIG. 22 is an example computer system useful for implementing various embodiments.

Various embodiments can be implemented, for example, using one or more computer systems, such as computer system 2200 shown in FIG. 22. Computer system 2200 can be any computer capable of performing the functions described herein.

Computer system 2200 includes one or more processors (also called central processing units, or CPUs), such as a processor 2204. Processor 2204 is connected to a communication infrastructure or bus 2206.

One or more processors 2204 may each be a graphics processing unit (GPU). In an embodiment, a GPU is a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 2200 also includes user input/output device(s) 2203, such as monitors, keyboards, pointing devices, etc., that communicate with communication infrastructure 2206 through user input/output interface(s) 2202.

Computer system 2200 also includes a main or primary memory 2208, such as random access memory (RAM). Main memory 2208 may include one or more levels of cache. Main memory 2208 has stored therein control logic (i.e., computer software) and/or data.

Computer system 2200 may also include one or more secondary storage devices or memory 2210. Secondary memory 2210 may include, for example, a hard disk drive 2212 and/or a removable storage device or drive 2214. Removable storage drive 2214 may be a floppy disk drive, a magnetic tape drive, a compact disk drive, an optical storage device, tape backup device, and/or any other storage device/drive.

Removable storage drive 2214 may interact with a removable storage unit 2218. Removable storage unit 2218 includes a computer usable or readable storage device having stored thereon computer software (control logic) and/or data. Removable storage unit 2218 may be a floppy disk, magnetic tape, compact disk, DVD, optical storage disk, and/any other computer data storage device. Removable storage drive 2214 reads from and/or writes to removable storage unit 2218 in a well-known manner.

According to an exemplary embodiment, secondary memory 2210 may include other means, instrumentalities or other approaches for allowing computer programs and/or other instructions and/or data to be accessed by computer system 2200. Such means, instrumentalities or other approaches may include, for example, a removable storage unit 2222 and an interface 2220. Examples of the removable storage unit 2222 and the interface 2220 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 2200 may further include a communication or network interface 2224. Communication interface 2224 enables computer system 2200 to communicate and interact with any combination of remote devices, remote networks, remote entities, etc. (individually and collectively referenced by reference number 2228). For example, communication interface 2224 may allow computer system 2200 to communicate with remote devices 2228 over communications path 2226, which may be wired and/or wireless, and which may include any combination of LANs, WANs, the Internet, etc. Control logic and/or data may be transmitted to and from computer system 2200 via communication path 2226.

In an embodiment, a tangible apparatus or article of manufacture comprising a tangible computer useable or readable medium having control logic (software) stored thereon is also referred to herein as a computer program product or program storage device. This includes, but is not limited to, computer system 2200, main memory 2208, secondary memory 2210, and removable storage units 2218 and 2222, as well as tangible articles of manufacture embodying any combination of the foregoing. Such control logic, when executed by one or more data processing devices (such as computer system 2200), causes such data processing devices to operate as described herein.

Based on the teachings contained in this disclosure, it will be apparent to persons skilled in the relevant art(s) how to make and use embodiments of the invention using data processing devices, computer systems and/or computer architectures other than that shown in FIG. 22. In particular, embodiments may operate with software, hardware, and/or operating system implementations other than those described herein.

CONCLUSION

It is to be appreciated that the Detailed Description section, and not the Summary and Abstract sections (if any), is intended to be used to interpret the claims. The Summary and Abstract sections (if any) may set forth one or more but not all exemplary embodiments of the invention as contemplated by the inventor(s), and thus, are not intended to limit the invention or the appended claims in any way.

While the invention has been described herein with reference to exemplary embodiments for exemplary fields and applications, it should be understood that the invention is not limited thereto. Other embodiments and modifications thereto are possible, and are within the scope and spirit of the invention. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments may perform functional blocks, steps, operations, methods, etc. using orderings different than those described herein.

References herein to "one embodiment," "an embodiment," "an example embodiment," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

The breadth and scope of the invention should not be limited by any of the above-described exemplary embodiments, but should be defined only in accordance with the following claims and their equivalents.

What is claimed is:

1. A method for building a community database of variant observations, comprising:
    receiving human variant datasets derived from samples generated by a plurality of distinct users, wherein the users consented to share pooled variant observations with other users;
    storing the received human variant datasets in a knowledge base of genomic information, wherein the knowledge base comprises an ontology data structure that identifies a causal relationship between a genetic variant and a phenotype based on a combination of the genetic variant and modifier variant information, wherein the knowledge base links the genetic variant and the modifier variant information, wherein the modifier variant information is based on curated evidence and derived from patient test information, and wherein the modifier variant information identifies whether modifier variants that modify a severity of the phenotype are likely to exist;
    searching the knowledge base to identify a plurality of variant observations that meet inclusion criteria for a pool;
    adding each identified variant observation to the pool;
    calculating one or more anonymized allele statistics from the pool; and
    classifying a variant observation in the pool into a clinical significance category using the knowledge base and the anonymized allele statistics of the pool,
    wherein at least one of the receiving, storing, searching, adding, calculating, or classifying are performed by one or more computers.

2. The method of claim 1, further comprising:
    determining that variant observations derived from one or more samples do not contribute to the pool of alleles based on at least one of a breadth of genome coverage of the sample, depth of coverage of the sample, quality of the sample, variant call quality, a phenotype associated with the sample, sample redundancy, variant counts, a trust metric for a source of the sample, community feedback, containing a well-established disease-causing variant, manual or automated quality control, or any combination thereof.

3. The method of claim 1, further comprising:
    annotating the samples with one or more ethnicities using at least one of principal component analysis, a user-provided annotation, or any combination thereof.

4. The method of claim 1, wherein the calculating comprises:
    calculating an allele frequency that is a ratio of a number of observed incidences of the given variant to a total number of samples in the pool believed to have potential to measure the given variant.

5. The method of claim 1, further comprising:
    providing to a user one or more allele statistics for one or more alleles.

6. The method of claim 5, further comprising:
    excluding access to the allele statistics from users who have not provided consent during the receiving step.

7. The method of claim 5, wherein the providing comprises:
    providing the allele statistics to the user via a web-based resource.

8. The method of claim 1, further comprising:
    filtering variants using the allele statistics.

9. The method of claim 1, wherein variant datasets are gathered during an interpretation workflow for variant datasets.

10. The method of claim 1, further comprising:
    providing an incentive to one or more of the users for sharing the variant datasets.

11. The method of claim 10, wherein the incentive is access to the allele statistics.

12. The method of claim 1, wherein the number of users is greater than 20.

13. The method of claim 1, wherein the number of users is greater than 50.

14. The method of claim 1, wherein the number of users is greater than 100.

15. The method of claim 1, wherein the number of users is greater than 1000.

16. The method of claim 1, wherein the number of aggregated samples is greater than 10,000.

17. The method of claim 1, wherein the number of samples is greater than 100,000.

18. The method of claim 1, wherein the number of samples is greater than 1,000,000.

19. The method of claim 1, further comprising:
    determining that variant observations in the plurality of variant observations do not contribute to the pool of alleles based on at least one of variant call quality, read depth, known association with a common technical error or failure mode, manual or automated quality control, or any combination thereof.

20. A system, comprising:
    a memory; and
    at least one processor coupled to the memory and configured to:
        receive human variant datasets derived from samples generated by a plurality of distinct users, wherein the users consented to share pooled variant observations with other users;
        store the received human variant datasets in a knowledge base of genomic information, wherein the knowledge base comprises an ontology data structure that identifies a causal relationship between a genetic variant and a phenotype based on a combination of the genetic variant and modifier variant information, wherein the knowledge base links the genetic variant and the modifier variant information, wherein the modifier variant information is based on curated evidence and derived from patient test information, and wherein the modifier variant information identifies whether modifier variants that modify a severity of the phenotype are likely to exist;

search the knowledge base to identify a plurality of variant observations that meet inclusion criteria for a pool;

add each identified variant observation to the pool;

calculate one or more anonymized allele statistics from the pool; and classify a variant observation in the pool into a clinical significance category using the knowledge base and the anonymized allele statistics of the pool.

21. The system of claim 20, wherein the at least one processor is further configured to:

determine that variant observations derived from one or more samples do not contribute to the pool of alleles based on at least one of a breadth of genome coverage of the sample, depth of coverage of the sample, quality of the sample, variant call quality, a phenotype associated with the sample, sample redundancy, variant counts, a trust metric for a source of the sample, community feedback, containing a well-established disease-causing variant, manual or automated quality control, or any combination thereof.

22. The system of claim 20, wherein the at least one processor is further configured to:

annotate the samples with one or more ethnicities using at least one of principal component analysis, a user-provided annotation, or any combination thereof.

23. The system of claim 20, wherein the at least one processor is further configured to calculate by:

calculating an allele frequency that is a ratio of a number of observed incidences of the given variant to a total number of samples in the pool believed to have potential to measure the given variant.

24. The system of claim 20, wherein the at least one processor is further configured to:

provide to a user one or more allele statistics for one or more alleles.

25. The system of claim 24, wherein the at least one processor is further configured to:

exclude access to the allele statistics from users who have not provided consent during the receiving step.

26. The system of claim 24, wherein the at least one processor is further configured to:

provide the allele statistics to the user via a web-based resource.

27. The system of claim 20, wherein the at least one processor is further configured to:

filter variants using the allele statistics.

28. The system of claim 20, wherein variant datasets are gathered during an interpretation workflow for variant datasets.

29. The system of claim 20, wherein the at least one processor is further configured to:

provide an incentive to one or more of the users for sharing the variant datasets.

30. The system of claim 29, wherein the incentive is access to the allele statistics.

31. A tangible computer-readable device having instructions stored thereon that, when executed by at least one computing device, causes the at least one computing device to perform operations comprising:

receiving human variant datasets derived from samples generated by a plurality of distinct users, wherein the users consented to share pooled variant observations with other users;

storing the received human variant datasets in a knowledge base of genomic information, wherein the knowledge base comprises an ontology data structure that identifies a causal relationship between a genetic variant and a phenotype based on a combination of the genetic variant and modifier variant information, wherein the knowledge base links the genetic variant and the modifier variant information, wherein the modifier variant information is based on curated evidence and derived from patient test information, and wherein the modifier variant information identifies whether modifier variants that modify a severity of the phenotype are likely to exist;

searching the knowledge base to identify a plurality of variant observations that meet inclusion criteria for a pool;

adding each identified variant observation to the pool;

calculating one or more anonymized allele statistics from the pool; and classifying a variant observation in the pool into a clinical significance category using the knowledge base and the anonymized allele statistics of the pool.

32. The computer-readable device of claim 31, the operations further comprising:

determining that variant observations derived from one or more samples do not contribute to the pool of alleles based on at least one of a breadth of genome coverage of the sample, depth of coverage of the sample, quality of the sample, variant call quality, a phenotype associated with the sample, sample redundancy, variant counts, a trust metric for a source of the sample, community feedback, containing a well-established disease-causing variant, manual or automated quality control, or any combination thereof.

33. The computer-readable device of claim 31, the operations further comprising:

annotating the samples with one or more ethnicities using at least one of principal component analysis, a user-provided annotation, or any combination thereof.

34. The computer-readable device of claim 31, the operations for calculating further comprising:

calculating an allele frequency that is a ratio of a number of observed incidences of the given variant to a total number of samples in the pool believed to have potential to measure the given variant.

35. The computer-readable device of claim 31, the operations further comprising:

providing to a user one or more allele statistics for one or more alleles.

36. The computer-readable device of claim 35, the operations further comprising:

excluding access to the allele statistics from users who have not provided consent during the receiving step.

37. The computer-readable device of claim 35, the operations further comprising:

providing the allele statistics to the user via a web-based resource.

38. The computer-readable device of claim 31, the operations further comprising:

filtering variants using the allele statistics.

39. The computer-readable device of claim 31, wherein variant datasets are gathered during an interpretation workflow for variant datasets.

40. The computer-readable device of claim 31, the operations further comprising:
   providing an incentive to one or more of the users for sharing the variant datasets.

41. The computer-readable device of claim 40, wherein the incentive is access to the allele statistics.

42. The method of claim 1, wherein the phenotype is associated with a disease.

43. The system of claim 20, wherein the phenotype is associated with a disease.

44. The computer-readable device of claim 31, wherein the phenotype is associated with a disease.

\* \* \* \* \*